United States Patent [19]
Forbes et al.

[11] Patent Number: 6,132,381
[45] Date of Patent: Oct. 17, 2000

[54] INTRAMYOCARDIAL ANOMALOUS ACTIVITY DETECTION BY SUBTRACTING MODELED RESPIRATORY EFFECT

[75] Inventors: A. Dean Forbes, Palo Alto; Eric D. Helfenbein, Sunnyvale, both of Calif.

[73] Assignee: Agilent Technologies, Inc., Palo Alto, Calif.

[21] Appl. No.: 08/911,089

[22] Filed: Aug. 14, 1997

[51] Int. Cl.$^7$ .................................. A61B 5/02; A61B 5/04
[52] U.S. Cl. .......................... 600/483; 600/509; 600/513
[58] Field of Search ..................................... 600/483, 508, 600/509, 513, 515, 519, 520, 521

[56] References Cited

U.S. PATENT DOCUMENTS

| | | | |
|---|---|---|---|
| 4,802,491 | 2/1989 | Cohen et al. | 600/515 |
| 5,148,812 | 9/1992 | Verrier et al. | 600/517 |
| 5,187,657 | 2/1993 | Forbes | 600/513 |
| 5,188,116 | 2/1993 | Pommrehn | 600/509 |
| 5,265,617 | 11/1993 | Verrier et al. | 600/517 |
| 5,348,020 | 9/1994 | Hutson | 600/509 |
| 5,437,285 | 8/1995 | Verrier et al. | 600/515 |
| 5,474,078 | 12/1995 | Hutson | 600/512 |
| 5,503,160 | 4/1996 | Pering et al. | 600/519 |
| 5,511,554 | 4/1996 | Helfenbein et al. | 600/519 |
| 5,570,696 | 11/1996 | Arnold et al. | 600/520 |
| 5,613,496 | 3/1997 | Arand et al. | 600/515 |
| 5,687,738 | 11/1997 | Shapiro et al. | 600/528 |
| 5,794,623 | 8/1998 | Forbes | 600/515 |

OTHER PUBLICATIONS

William H. Hutson, "High–Resolution Subspace Techniques for Cardiac Analysis", Oct. 24–26, 1995, vol. 1, pp. 230–238, Proceedings of the 6th International Conference on Signal Processing Applications & Tech, Boston, MA.

Ichiro Watanabe et al., "Two Types of ST–T Alternans During Acute Myocardial Ischemia in the In–situ Pig Heart", 1995, vol. 92(8), pp. I–640, Circulation.

Richard T. Behrens, "Signal Processing Applications of Oblique Projection Operators", 1994, vol 42(6), pp. 1413–1423, IEEE Transactions on Signal Processing.

Richard L. Verrier, "Electrophysiologic Basis for T Wave Alternans as an Index of Vulnerability to Ventricular Fibrillation", 1994, vol. 5(5), pp. 445–461, Journal of Cardiovascular Electrophysiology.

David S. Rosenbaum, et al., "Electrical Alternans and Vulnerability to Ventricular Arrhythmias", 1994, vol. 330(4), pp. 235–241, The New England Journal of Medicine.

Alle–Jan Van Der Veen, et al., "Subspace–Based Signal Analysis Using Singular Value Decomposition", 1993, vol. 81(9), pp. 1277–1308, Proceedings of the IEEE.

William H. Press, et al.,Numerical Recipes in C: The Art of Scientific Computation , 2nd Ed., 1992, p. 66, Cambridge University Press, Cambridge, MA.

(List continued on next page.)

Primary Examiner—Cary O'Connor
Assistant Examiner—Navin Natnithithadha

[57] ABSTRACT

A technique of detecting repeating patterns of anomalous intramyocardial Wenckebach electrical activity in a patient is provided. The method of the technique deals with determining the presence or absence of such intramyocardial anomaly by processing signals that are electrical potential signals which include a cardiac component and a respiratory component. The method includes estimating the respiratory component (preferably by a regression curve-fitting technique based on data of the electrical potential signals and data of respiratory signals), finding the difference between the electrical potential and the estimated respiratory component and based on this difference inferring the presence of absence of the intramyocardial anomaly. Preferably, a generalized inverse of a matrix representing Wenckebach basis functions reflecting Wenckebach phases and modes is used to act on a vector representing the difference between the electrical potential and the estimated respiratory component to determine whether any repeating intramyocardial electrical anomaly is present.

28 Claims, 13 Drawing Sheets

OTHER PUBLICATIONS

John N. Amoore, et al., "Respiration and the ECG: A Study Using Body Surface Potential Maps", 1988, vol. 21(3), pp. 263–271, *Journal of Electrocardiology*.

D. Leigh Carson, et al., "Characterisation of Unipolar Waveform Alternation in Acutely Ischaemic Porcine Myocardium", 1986, vol. 20, pp. 521–527, *Cardiovascular Research*.

Virginia C. Klema et al., "The Singular Value Decomposition: its Computation and Some Applications", 1980, vol. AC–25(2), pp. 164–176, *IEEE Trans. Automat. Contr.*

Rosenbaum et al., "Predicting Sudden Cardiac Death from T Wave Alternans of the Surface Electrocardiogram: Promise and Pitfalls", 1996, vol. 7(11), pp. 1095–1111, *J. of Cardiovascular Elect.*

Hutson, "High–Resolution Subspace Techniques for Cardiac Analysis", 1995, vol. 1, pp. 230–238, *The Proc. of the 6th Intl. Conf. on Signal Proc. Appl. & Tech.*

Verrier et al., "Electrophysiologic Basis for T Wave Alternans as an Index of Vulnerability to Ventricular Fibrillation", 1994, vol. 5(5), pp. 445–461, *J. of Cardiovascular Electrophysiology*.

Van Der Veen et al., "Subspace–Based Signal Analysis Using Signular Value Decomposition", 1993, vol. 81 (9), pp. 1277–1308, *Proc. of the IEEE*.

Rosenbaum et al., "Elect. Alternans & Vulnerability to Ventribular Arrhythmias", 1994, vol. 330(4), pp. 235–241, *The New England J. of Med.*

Carson et al., "Characterisation of Unipolar Waveform Alternation in Acutely Ischaemic Porcine Myocardium", 1986, vol. 20, pp. 521–527, *Cardiovascular Research*.

Hogg et al., "On Adaptive Estimation", 1984, vol. 9, pp. 333–343, *J. of Stat. Planning & Inference (N. Holland)*.

Klema et al., "The Singular Value Decomposition: Its Computation and Some Applications", 1980, vol. AC–25 (2), pp. 74–86, *IEEE Trans. on Auto. Control*.

Haykin, "Adaptive Filter Theory", 2nd Ed., pp. 409–411, Prentice Hall Englewood Cliffs, NJ 07632.

Scharf, Univ. of CO at Boulder, "Statistical Signal Processing", pp. 136–149, Addison–Wesley Pub. Co.-

Constant:
Period Two:
Period Three:
Period Four:
Period Five:

INTRAMYOCARDIAL ANOMALOUS ACTIVITY DETECTION BY SUBTRACTING MODELED RESPIRATORY EFFECT

FIELD OF THE INVENTION

The present invention is related to anomalous myocardial activity of the heart of a person or an animal, more particularly to the detection of intramyocardial Wenckebach activity.

BACKGROUND

Wenckebach Activity

Of the 400,000 sudden cardiac deaths (SCD) that occur in North America annually, sixty percent occur without any recognized warning. However, even among individuals in the top decile of SCD risk, each year only a small percentage die due to SCD. Potential SCD victims are indistinguishable from the rest of high risk individuals by present methods of analysis. Furthermore, a sizable majority of SCD victims (60%) are not even in the top decile of risk. There is currently no known way of targeting aggressive therapies at the small percentage of high risk subjects who will be SCD victims within any given year.

SCD typically results from the interplay of three underlying factors: myocardial vulnerability, electrical instability, and neuroendocrine activation. However, any single factor may suffice to produce SCD.

Classically, risk factor analysis has been used to identify those at elevated risk of SCD. In recent years, to improve SCD risk assessment, researchers have introduced purportedly direct measures of cardiovascular instability and related these to the incidence of SCD. Since most of the proposed measures focus on only one of the many factors underlying SCD, the raw measures provide (statistically) marginal analyses and hence tend to be inadequate for diagnostic purposes.

To some extent, improper test marginality can be overcome through the proper choice of the measurement context. For example, a patient recovering from a recent myocardial infarction will most likely have a pathologically heterogeneous myocardial substrate. Exercising that patient will superimpose neuroendocrine activation. The electrical instability factor can then be studied.

Experiments on myocardial cells show that metabolically compromised tissue may respond to stimuli in a patterned manner. Such patterns in the electrocardiogram (ECG) should be directly related to electrical instability and may be more predictive of SCD than currently used non-invasive clinical ECG analysis methods. One form of patterned behavior is T-wave alternans, which has been studied as related to ventricular fibrillation. See, e.g., D. S. Rosenbaum et al., "Electrical Alternans and Vulnerability to Ventricular Arrhythmias," *NEJM* 330(4): 1994, 235–241; R. L. Verrier and B. D. Nearing, "Electrophysiologic Basis for T Wave Alternans as an Index of Vulnerability to Ventricular Fibrillation," J Cardiovasc *Physiol* 5: 445–461, 1994; I. Watanabe et al., "Two Types of ST-T Alternans During Acute Myocardial Ischemia in the In-Situ Pig Heart," Circ 92(8): I-640, 1995; and D. L. Carson et al., "Characterization of unipolar waveform alternation in acutely ischaemic porcine myocardium." Cardiovasc Res 20: 521–527, 1986.

T-wave alternans appears in the body-surface ECG as a patterned beat-to-beat variation in the T-wave of ECG waveforms (FIG. 2A and G. H. Mudge, Jr., Manual of Electrocardiography, Boston: Little, Brown, and Co., 1986). It involves voltage levels in the T-wave that switch between two values on alternate beats: high, low, high, low, and so on.

Intramyocardical Wenckebach activity is another form of patterned beat-to-beat variability, but can be more complex than alternans. The term "Atrio-ventricular (A-V) Wenckebach behavior" in cardiology commonly refers to a cardiac arrhythmia in which the conduction system fails to begin depolarization of the ventricles in a patterned manner (for example, failing on every other, or every third, beat). "Intramyocardial Wenckebach behavior" refers to repeating patterns of anomalous electrical activity within the ventricles, due to the patterned failure of (localized) regions of myocardium to depolarize. These regions are usually ischemic, compromised due to lack of an adequate oxygen supply.

In both traditional Wenckebach and intramyocardial Wenckebach anomalies, a repeating stimulus travels through the heart to metabolically (and thus electrically) compromised tissue. This tissue responds to each stimulus by depolarizing (and thus conducting the stimulus) until it becomes electrically fatigued. It then fails to respond to one or more stimuli until it recovers, at which time it responds to the next arriving stimulus. The behavior then repeats. This patterned activity can be specified by a code involving a pair of integers, M:N. The first integer gives the periodicity of the pattern, i.e., how many trigger events occur before the cycle begins afresh; the second integer tells how many times the electrically compromised tissue responds before it fatigues and fails. Thus, for example, a 4:3 Wenckebach pattern has a period of four beats with the tissue responding to three of the stimuli before it fails: respond, respond, respond, fail; respond, respond, respond, fail; . . . and so on. As a voltage phenomenon, T-wave alternans mimics 2:1 Wenckebach activity, but is localized to the T-wave. Hence, a technique that can detect 2:1 Wenckebach activity can also detect alternans.

Whereas the common form of atrial-ventricular (A-V) Wenckebach behavior is readily apparent on the body-surface ECG, intramyocardial Wenckebach manifests itself as small, anomalous, beat-to-beat electrical potential variations buried in much larger normal variations due to respiration and noise. Respiration modulates the ECG due to the physical movement of the heart (which rests on the diaphragm) relative to the recording electrodes; it affects conductivity within the thorax; it causes variations of heart size due to its effect on cardiac filling. Respiration is the largest source of interference. Noise sources include superimposed muscle tremor noise (EMG), gastric electrical activity (electrogastrogram, EGG), and electromagnetic interference (EMI). Detection of intramyocardial Wenckebach activity is further complicated when an affected region of the heart switches from one Wenckebach pattern to another and when multiple regions exhibit disparate, even competing, Wenckebach patterns.

Investigation of alternans activity (as it relates to susceptibility to sudden cardiac death) has been reported by two university groups: Massachusetts Institute of Technology (MIT) and Georgetown University. See, e.g., D.S. Rosenbaum et al., Supra.; U.S. Pat. No. 4,802,491; U.S. Pat. No. 5,148,812; and U.S. Pat. No. 5,437,285. In the MIT method, the incidence and extent of T-wave alternans was estimated by steps including formation of a spatial magnitude vector, identification of and aligning 128 T-waves each of 150 msec duration, and Fast Fourier transformation (FFT) of each epoch of the T-waves. The MIT group has a paper discussing the analysis for alternans while the patient is pedaling at one-third the heart rate (D. S. Rosenbaum et al., "Predicting Sudden Cardiac Death from T Wave Alternans of the Surface Electrocardiogram: Promises and Pitfalls," *J Cardiovasc.*

*Electrophysiology*, 7: 1095–1111, November 1996). In U.S. Pat. No. 5,570,696, the MIT group describes a method for assessing myocardial electrical stability by increasing heart rate to provoke alternans behavior. In the Georgetown method, data were analyzed via the method of complex demodulation. The Georgetown group attributes T-wave alternation to the cellular monophasic action potential duration alternans phenomenon, not to gap junction failure (the mechanism originally put forward by the MIT group). Thus far, prior art techniques are not well suited to the detection of mixtures of Wenckebach activity.

Subspace Filtering Methodology

When modem signal analysts are required to extract a subtle signal from a timeseries corrupted by interference and noise, a useful technique is "subspace filtering." See, e.g., V. C. Klema and A. J. Laub, "The Singular Value Decomposition: Its Computation and Some Applications," *IEEE Trans AC* 25 (2): 164–176, 1980; A-J van der Veen et al., "Subspace-Based Signal Analysis Using Singular Value Decomposition," *Proc IEEE* 81 (9): 1277–1308, 1993.

In subspace filtering, a given timeseries is viewed as a vector in a multi-dimensional space. The technique seeks to determine a subspace that contains the signal part of the timeseries while being orthogonal to the interference and noise. The basis vectors of the full vector space, as well as its subspaces, are typically determined using linear algebra's well-known method of singular value decomposition (SVD). Expanded in terms of the basis vectors of the signal subspace, the signal emerges from the obscuring interference and noise.

Subspace filtering for compression of the electrocardiogram (ECG) data was investigated more than two decades ago. It was assumed that the basis vectors corresponding to the smallest singular values would correspond to noise. Recently, W. H. Hutson applied subspace filtering methods to ECG signals by suppressing interference to detect both altemans and late potentials. See W. H. Hutson, "High-Resolution Subspace Techniques for Cardiac Analysis," *Proceedings of the Int. Conf On Sig Proc. Appl.* and Tech. 1995: 230–238; and W. H. Hutson, U.S. Pat. No. 5,474,078.

U.S. patent application Ser. No. 08/722,351, Attorney Docket No. 10960792-1, commonly assigned with the assignee of the present application, discloses a subspace analysis technique applied to analyze Wenckebach activity. In that 08/722,351 application, which is incorporated by reference in its entirety herein, the respiratory interference subspace is oblique to the Wenckebach subspace and the noise subspace. A Wenckebach matrix is used to treat, in parallel, signals from the Wenckebach activity and the respiratory interference. What is needed is a technique that can analyze for Wenckebach activity, including altemans activity, without the necessity of using such an oblique treatment.

SUMMARY

In the present invention, an embodiment provides a technique for the non-invasive detection of intramyocardial Wenckebach behavior in the ventricles of the human heart.

An embodiment of the technique for detecting intramyocardial Wenckebach behavior includes acquiring electrical potential data that include a cardiac component and a respiratory component, as well as additive noise from various physiological and non-physiological sources; filtering to remove the noise and baseline wander; estimating and suppressing the respiratory component; and detecting and estimating the presence and strength of anomalous intramyocardial Wenckebach patterns.

In one embodiment, the electrical potential data are body surface potentials (BSP).

In a preferred embodiment, the respiratory component is estimated by regressing the electrical potential data on respiratory data (simultaneously acquired from the subject) to model the interaction between them. Calculating a regression model using a linear or non-linear regression technique is akin to curve-fitting data points to obtain a surface equation that represents the respiratory component of the BSPs. Once the respiratory component is obtained, it can be subtracted from the BSPs to obtain data that reflect the residual cardiac components substantially without the respiratory interference. To what extent the respiratory effects can be removed will depend on how well the regression model represents the actual interaction of respiration on the underlying cardiac data and how much noise is still present after initial filtering.

To determine the presence or absence of intramyocardial Wenckebach behavior, a set of basis functions is generated, which represent the different Wenckebach patterns that are to be detected. Since there are, theoretically, an infinite number of possible Wenckebach patterns, a subset of patterns is chosen to represent only the most likely cases. In general, basis functions are a set of functions, linear combinations of which can be used to approximate other functions. A well-known example of basis functions are the sines and cosines used in Fourier analysis to expand a function as a Fourier series—sums of appropriately weighted sines and cosines. Here, an attempt is made to represent the beat-to-beat cardiac variations (which remain after the respiratory variations are removed) as a linear combination of the Wenckebach basis functions. This, generally, is equivalent to a search for the chosen Wenckebach patterns in the cardiac data. If one or more Wenckebach patterns are indeed present, their repeated nature allows them to be detected in the presence of remaining respiratory interference and noise. The weights calculated for the basis functions will indicate the intensity of each Wenckebach pattern.

In one embodiment, this invention provides an apparatus for detecting repeating patterns of anomalous intramyocardial electrical activity, i.e., intramyocardial Wenckebach activity, in the heart of a patient. The apparatus includes a device for obtaining data on electrical potentials that include a cardiac component and a respiratory component; a device for obtaining respiratory data from the body; and a processor electrically associated with the above two devices to estimate the respiratory component in the electrical potential and to find the difference between the electrical potential data and the estimated respiratory component. Based on this difference and a set of patterns (the modes and phases) of Wenckebach anomalies, the processor determines the presence or absence of intramyocardial anomalous electrical activity.

The present technique can be advantageously used to determine whether intramyocardial anomalous electrical activity is present, including alternans and Wenckebach activity other than alternans, as well as mixtures of such anomalous Wenckebach activities. Because not all electrical instabilities are alternans, the technique of the present invention is advantageous over prior art methods that are suitable only for detecting alternans.

In the technique of the present invention, the assessment of whether Wenckebach activity has occurred is done serially, i.e., by reducing respiratory interference and noise from BSP data before analyzing it for Wenckebach patterns. This greatly simplifies the mathematics of the analysis.

Further, unlike prior art frequency domain techniques for analyzing alternans, the technique of the present invention operates in the time domain, which allows robust methods for inferring the presence of Wenckebach activity to be used. In addition, because the technique of the present invention operates in the time domain, removal of bad or inappropriate data is relatively straightforward. This is advantageous because anomalous beats introduce great mathematical difficulties into frequency-domain methods.

BRIEF DESCRIPTION OF THE DRAWINGS

The following figures are included to better illustrate the embodiments of the apparatus and technique of the present invention. In these figures, like numerals represent like features in the several views.

DETAILED DESCRIPTION OF THE INVENTION

Figure 1:
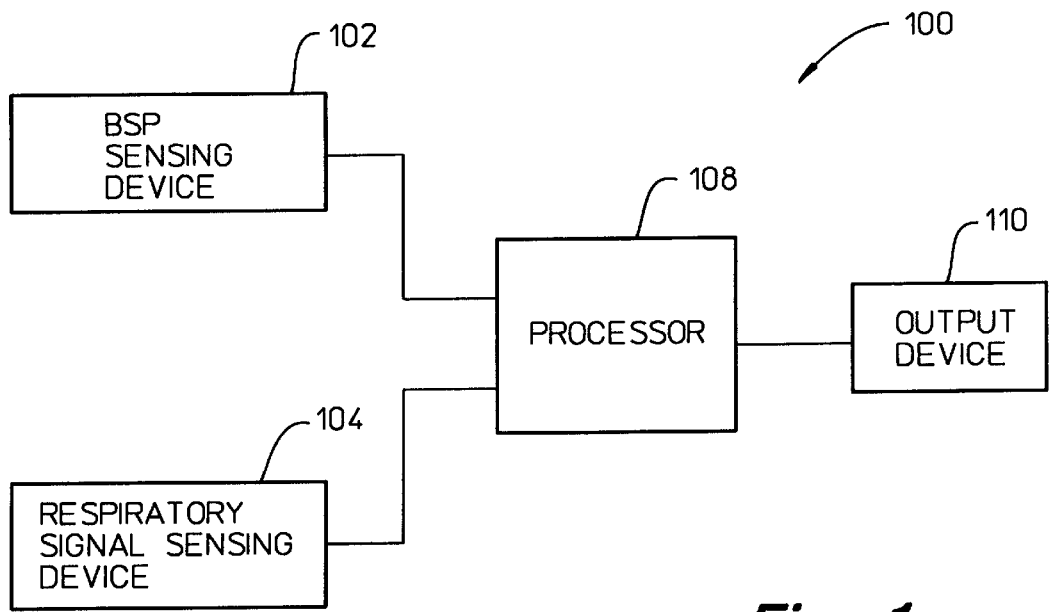
FIG. 1 shows an embodiment of the apparatus of the present invention.

FIG. 1 shows an embodiment of the apparatus of the present invention for detecting repeating (or cyclical) anomalous intramyocardial activity. As used herein, the term "anomalous intramyocardial activity" refers to the failure of intramyocardial tissue to respond to a triggering stimulus. In "repeating" or "cyclical" anomalous intramyocardial activity, the pattern of response and failure to respond to stimuli repeats in a periodic fashion. Such behavior is referred to herein as intramyocardial Wenckebach behavior.

Figure 2A:
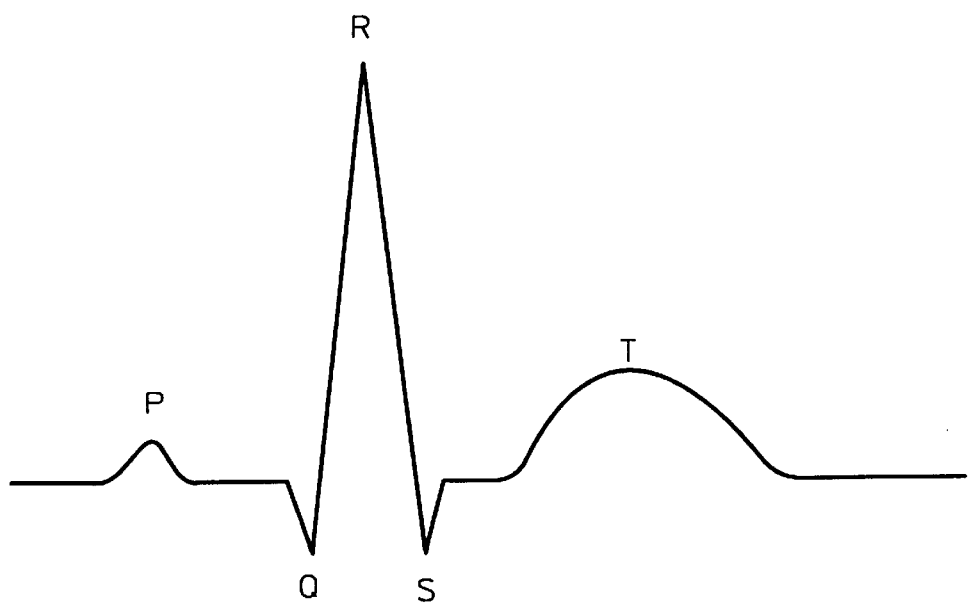
FIG. 2A shows a BSP signal detected from a human subject, showing the P, QRS, and T waves.

In FIG. 1, the apparatus 100 includes a device 102 for sensing, i.e., measuring, body surface potentials (BSP) and a device 104 for sensing, i.e., measuring, respiratory signals. The BSP signals are electrical potentials generated mainly by the heart sensed from the body. A very common example of BSP is the signal traditionally called "ECG signal" sensed by electrodes placed on the surface of the skin on the body about the torso. Commonly used equipment for sensing and recording "ECG signals" can be used. Such equipment may include electrodes, wires, amplifiers, filters, A/D converters, etc. It is noted that, for convenience sake, electrical signals reflecting the electrical activity of the heart, measured by electrodes placed inside the body, are also called BSP herein. Examples include electrical potentials resulting from electrodes placed in the esophagus or inside the chest on the heart, or in a coronary vein or cardiac chamber. A typical BSP for a human subject is shown in FIG. 2A.

For sensing respiratory signals, methods commonly used for that purpose are suitable. For present purposes, transthoracic respiratory impedance (RI) can be used as an illustrative example of respiratory signals. An alternative technique for measuring respiration is by analyzing the muscle tremor from BSP signals, e.g., those typically called "ECG" signals recorded from the body (see U.S. patent application Ser. No. 08/769,557, Attorney Docket Number 10960801-1, which is commonly assigned to the same assignee with the present application, said U.S. Ser. No. 08/769,557 application is incorporated by reference in its entirely herein). From different BSP electrodes, different estimates of the respiratory signal can be obtained. Other methods for gauging respiration that can be used include, e.g., nasal thermistor, strain gauge on the chest, pneumotach, and the like. From such respiration measurements, a waveform can be obtained to represent the respiration of the patient.

The BSP signal-sensing device 102 and the respiratory signal-sensing device 104 are electrically connected to a processor 108 for processing the signals from the devices 102 and 104. Devices for sensing BSP and respiratory signals are widely known in the art. Examples of such devices include, but are not limited to, ECG electrodes and RI electrodes that can be positioned at appropriate locations on a patient. If preferred, the RI electrodes can be the same ECG electrodes that measure the "ECG" signals, except that a high frequency (higher than the frequency of "ECG" signals) current is injected between the RI electrodes to result in the voltage of the RI signals. The signals from the electrodes can be passed through amplifier(s) before being processed by the processor 108. Alternatively, the processor can have amplifier(s) for amplifying the signals. Also, analog or digital filters can be used for filtering noise before processing the signals with the processor 108. Furthermore, the respiratory signals can be extracted from voltage fluctuations due to muscle tremors in the BSP signals, in which case, the electrodes for sensing the respiratory signals will be the same as those for sensing the BSP signals.

The processor 108 can be an electronic digital computer, network computer, microprocessor, and the like, that has memory for storing data and which can perform matrix operations. Preferably, there is an output or display device 110 such as printer, CRT display, plotter, and the like, for interfacing with a human operator. The processor can be controlled by a program (i.e., computer program code) having the algorithm to determine the presence or absence, as well as the magnitude, of Wenckebach activity. The program has a code to coordinate the flow of information of the various devices, such as the processor, display device, BSP signal collection, respiratory signal collection, matrix operations, and the like, for determining the presence or absence, and magnitude of the Wenckebach activity from the BSP and respiratory signals. All or part of the program can be stored in the processor or imported (or read) into the processor by means of electrical wires and storage devices such as hard disks, floppy disks, magnetic tapes, compact disks, and the like, in which all or part of the program are stored.

The BSP signals measured from the body of a patient may consist of components due to normal cardiac conduction, anomalous (e.g., Wenckebach) activity, muscle tremor noise (EMG), electromagnetic interference (EMI), electrogastric interference (EGG), and modulative interference due to respiration. Hereinafter, the term "interference" refers to the structured electrical interference due to respiration unless specified otherwise. The other electrical noise of noncardiac origin, including electrical noise due to electromagnetic interference, electrogastric noise, and muscle tremor, are referred to as "noise." Preferably, the EMI, the EGG, and the muscle tremor noise are suppressed or reduced by applicable techniques. As a result, the search for intramyocardial Wenckebach behavior will be primarily affected by the substantial interfering effects of respiration. When respiration is shallow, respiratory interference may be taken to be additive, i.e., in the BSP the voltage of the respiratory interference is additive to the voltage due to the voltage purely of cardiac origin. To facilitate understanding of the present invention, for practical purposes, one can assume that the Wenckebach signal and respiratory interference vector subspaces are usually mutually orthogonal, i.e., they are usually but not necessarily always independent of each other.

This invention detects repeated patterns of anomalous intramyocardial Wenckebach activity by appropriately reducing the respiratory interference from sensed BSP signals. In one aspect, the present invention uses a technique of modeling the respiratory interference in filtered BSP signals by regressing the filtered BSP data on respiratory data to extract that part of the BSP data attributable to respiration. It is preferred that all non-respiratory sources of noise be removed before regression.

Filtering the raw BSP

In an embodiment of the present invention the raw BSP data are collected from the patient's body and are then filtered to reduce noise from various sources before respiratory interference is removed. The filtering steps involve: detection of QRS complexes; filtering to remove electromagnetic interference (EMI); removing baseline wander and gastric muscle noise (EGG); and averaging for reduction of muscle artifact (EMG) and remaining EMI. The filtering steps may be performed on the raw analog signals, or on suitably digitized versions.

The location of QRS complexes are identified in the raw BSP data. Many automated algorithmic methods are available for this purpose.

To reduce the noise caused by EMI (e.g., noise radiated by the electrical power line), analog or digital filters can be used. For example, the "sinusoidal trend filter" described in U.S. patent application Ser. No. 08/624,194, Attorney Docket No. 10951188-1, filed Mar. 28, 1996, can be used, which patent application is incorporated by reference in its entirety herein.

Techniques for reducing baseline wander (which may be due to electrode motion artifact and/or gastric muscle noise) are known in the art, and may be employed for this purpose. One method involves fitting cubic splines to the BSP to estimate the baseline wander. This estimate is then subtracted from the filtered BSP data. On cubic splines in general, see, e.g., W. H. Press et al., *Numerical Recipes in C: The Art of scientific Computation*, Second Edition, Cambridge, Cambridge University Press, 1992, 66, which is incorporated by reference herein. In the present context, beat on sets are used as the knots (points the spline must pass through) in the cubic spline method of Press et al.

In the description of this embodiment, although the filtering steps are specified in a particular sequence, it is to be understood that they may be performed in a different order.

Once EMI and baseline wander are removed, the QRS onset point is re-identified for each beat. The onset represents the first appearance of ventricular depolarization in the ECG. This point can then be used as a reference point in the next steps. Template matching or other suitable techniques that are known to those versed in the art may be employed for this purpose.

Starting at the onset point on each beat, the QRST complex is divided into a number of adjacent short time intervals, e.g., each 5 msec. in duration. These intervals are referred to as "time bins." The filtered BSP data that fall into each time bin are averaged so that one value is computed for each bin. Averaging adjacent BSP data samples in this manner serves to reduce the effects of muscle tremor noise, as well as reducing residual EMI that has survived EMI filtering. Overlapping (versus adjacent) time bins may alternatively be employed.

The averaged values for the time bins are placed in a matrix, herein called Y. Each row of Y, contains the values that span one QRST complex, from onset past the end of the T-wave. The first row contains the values from the first beat, the second row contains those from the second beat, etc. In summary, Y(i,j), representing the value at the with row and jth column in the Y matrix, will contain the average value from the jth time bin for the ith beat. Y will have the form shown below:

$$Y = \begin{bmatrix} Y(1,1) & Y(1,2) & Y(1,3) & Y(1,4) & Y(1,5) & \text{-----} \\ Y(2,1) & Y(2,2) & Y(2,3) & Y(2,4) & Y(2,5) & \text{-----} \\ Y(3,1) & Y(3,2) & Y(3,3) & Y(3,4) & Y(3,5) & \text{-----} \\ \text{-----} \\ \text{-----} \\ \text{-----} \\ \text{-----} \\ \text{-----} \end{bmatrix}$$

In the above array representation of Y, "- - - -" represent the other unspecified elements in the matrix.

Each column of the matrix Y, containing values corresponding to a given time bin after QRS onset, spans the set beat to be used in a study. Each vector y discloses the beat-to-beat levels of electrical activity (for its corresponding interval of time after the onset of cardiac depolarization), contaminated by respiratory interference. Buried in this "beat-series" is the Wenckebach pattern, if indeed myocardial Wenckebach behavior is present. (The term "beat series" will be used herein to refer to a vector containing a series of values, each value corresponding to one beat in a series of consecutive beats. Each value is sampled at a fixed delay from a reference point on the QRS complex, e.g., from QRS onset).

The next section describes how regression is used to remove the respiratory interference effects.

Removal of Respiratory Interference

As previously stated, in an embodiment of the present invention, to analyze for intramyocardial Wenckebach behavior in the filtered beat-series data, the effects of respiratory interference must be removed (or significantly reduced). This can be accomplished by regressing the filtered BSP data on simultaneously acquired respiratory data to model the interaction between them. Once the respiratory component is obtained via the model, it can be subtracted from the filtered BSP data to obtain cardiac data that have most of the respiratory interference removed. This regression residual will contain intramyocardial Wenckebach patterns, if present, in addition to noise that has survived the filtering and regression procedures. The regression residuals will hereafter be referred to as the "cardiac signature," since it will contain a Wenckebach "signature" if Wenckebach activity is present.

As used herein, the term "regress" or "regression" refers to fitting a parametric surface to a set of data points so as to obtain the best fit between the surface and the data. The regression residuals refer to the difference between the modeled and actual data points. As a well known regression example, a straight line can be fitted to a set of data vectors x and y to obtain a linear equation y=ax+k where a and k are constants chosen to obtain the best fit according to a specified error criterion for the residuals. Numerous methods employing different error criteria exist for solving regression equations. For example, a least squares regression method will minimize the sum of the squared residuals. A least absolute deviation method will minimize the sum of the absolute values of the residuals.

In the present invention, various methods and models can be used to regress the filtered BSP data against the respiratory data, i.e., fit data points from the filtered BSP data to the surface defined by the respiratory data to obtain a model of the respiratory effects. For example, in a simple model, let y be a column of the matrix Y (as specified in the previous section) containing a beat series of filtered BSP data for a given time bin. Let r represent a vector of respiratory data containing values of a respiratory waveform sampled simultaneously to the time bins in y. Then the respiratory data points r can be fitted to the values in y using an equation of the form y=ar+k, where a and k are constants to be determined by the regression method.

The regression fit may be improved if differently acquired respiratory waveforms are included in the regression, since multiple waveforms will contain ancillary information with respect to respiration. For example, respiration waveforms extracted from muscle tremor in the BSP may be combined with respiration waveforms from impedance, strain gauge, pneumotach devices, and the like. Another approach uses more than one signal lead of a particular method so that each lead provides a different time series representing respiration. In these cases, the regression equation may be written as $y=a_1r_1+a_2r_2+a_3r_3+ \ldots +a_jr_j+k$, where each vector $r_j$ contains a respiratory series from a different source, and each $a_j$ and k are constants to be determined by the regression method.

The process of respiration can be divided into three distinct phases, namely, inspiration, expiration, and rest. Respiration affects the BSP differently during each of these phases. To include these physiological effects in the regression equation, the phase of respiration at each beat may be encoded in additional vectors p, q, etc. for inclusion in the equation, e.g., $y=a_1r_1+a_2r_2+a_3r_3+ \ldots +a_jr_j+k+p+q+ \ldots$ .

Another possible extension is that there are theoretical as well as experimental grounds for including a quadratic dependence on respiration. In this case the equation will be of the form $y=a_1r_1+c_1r_1^2+a_2r_2+c_2r_2^2+ \ldots +a_jr_j+c_jr_j^2+k+p+q+ \ldots$ where each $c_j$ is a weight for its quadratic term $r_j^2$.

Figure 2B:
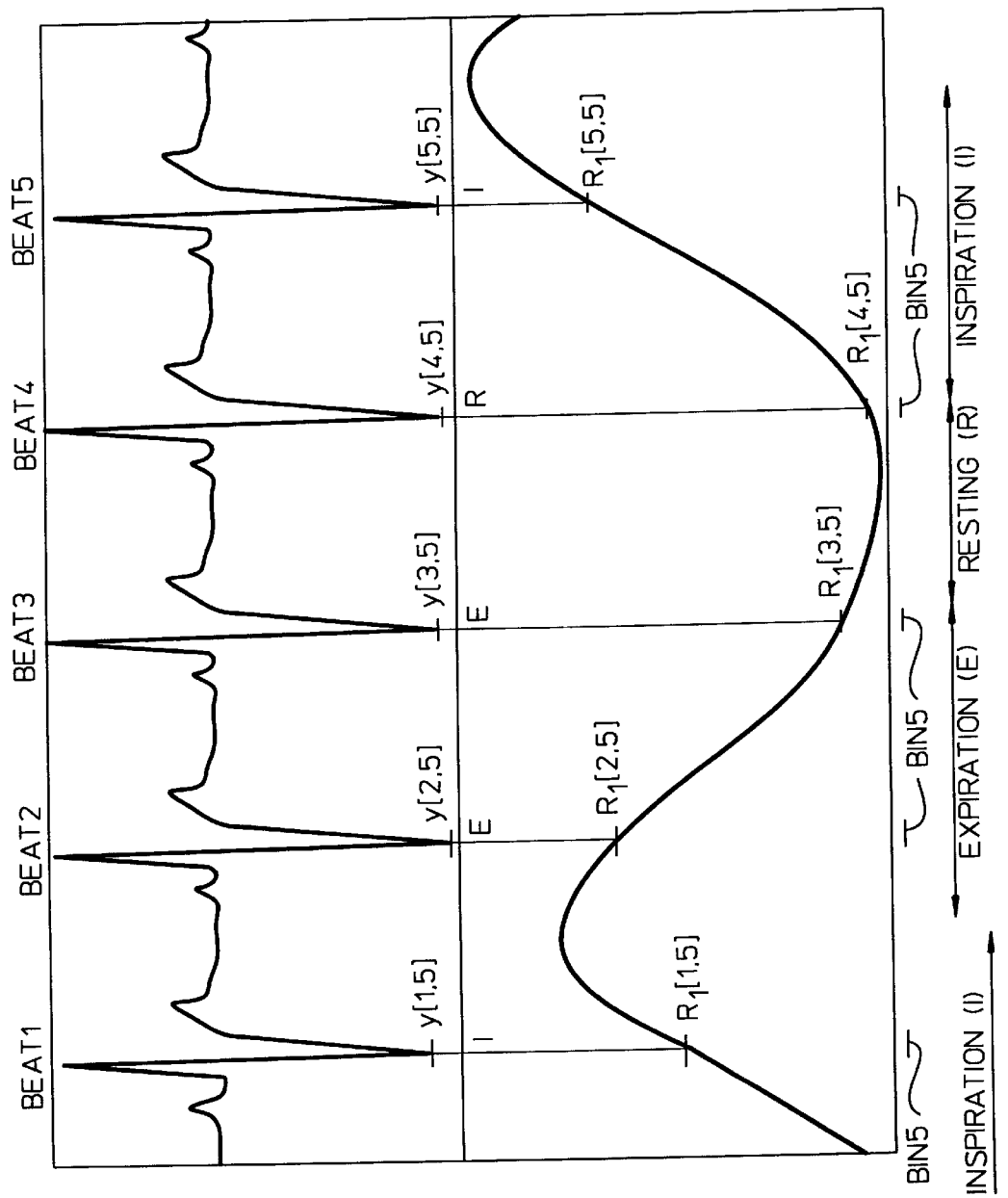
FIG. 2B illustrates how values for the BSP matrix Y and the respiratory matrix R are obtained from filtered BSP and respiratory signals.

To obtain the time series for implementing the procedure to remove respiratory interference from the filtered BSP data, the respiratory signals (e.g., from respiratory impedance, BSP muscle tremor, pneumotach, etc., ) are measured from the patient's body simultaneously with the BSP measurements. The respiratory signals can be filtered, e.g., with a Physiological Event Time Averaging (PETA) filter (see, Pering et al., U.S. Pat. No. #5,503,160 and U.S. Pat. No. #5,511,554), to remove cardiogenic artifacts. Corresponding to the averaged value of the filtered BSP for each time bin in each beat there will be a value for each representation of respiration. This is illustrated in FIG. 2B. In FIG. 2B, the top tracing is the filtered BSP signal and the bottom waveform is the first respiratory waveform. In the BSP tracing, the averaged value for the fifth time bin is labeled for the first five beats. The corresponding values of the respiration waveform are also labeled. The respiratory values corresponding to each time bin on each beat are placed in a matrix $R_1$. Each row of $R_1$ represents the values of the respiratory data for a given beat, spanning the various time bins. Each column of $R_1$ represents a respiratory beat series (i.e., respiratory data sampled once per heartbeat) for a given time bin, spanning the various beats.

$$R_1 = \begin{bmatrix} R_1(1,1) & R_1(1,2) & R_1(1,3) & R_1(1,4) & R_1(1,5) & \text{-------} \\ R_1(1,1) & R_1(1,2) & R_1(1,3) & R_1(1,4) & R_1(1,5) & \text{-------} \\ R_1(1,1) & R_1(1,2) & R_1(1,3) & R_1(1,4) & R_1(1,5) & \text{-------} \\ \text{------------------------------------------------------} \\ \text{------------------------------------------------------} \\ \text{------------------------------------------------------} \\ \text{------------------------------------------------------} \\ \text{------------------------------------------------------} \end{bmatrix}$$

The filtered BSP matrix Y and the respiration matrix $R_1$ both hold numbers, representing amplitude of signals. However, as previously mentioned, there is a further non-voltage aspect of respiration, namely, the phase of respiration, that preferably is included because the physiology and hence bioelectric potential of the heart differs among inspiration, expiration, and rest. The value of the respiratory waveform at a given point does not encode these phase differences. Thus, a further (symbol-containing) array, Q, is defined here. If a time bin of a beat occurs during inspiration, the appropriate cell of Q holds an "I"; if expiration, an "E"; if resting, an "R". The array Q, depending on the specific respiration of the patient, has a form that looks like the following illustrative array:

$$Q = \begin{bmatrix} \text{------} & I & \text{------} \\ \text{------} & E & \text{------} \\ \text{------} & E & \text{------} \\ \text{------} & R & \text{------} \\ \text{------} & I & \text{------} \\ \text{------------------} \\ \text{------------------} \\ \text{------------------} \end{bmatrix}$$

Each row represents the respiratory phase data for a given beat for the various time bins; each column represents the respiratory phase data for a given time bin for the various beats. In the above illustrative array, for clarity by simplicity, the "--------" symbols represent the letters I, B, R, and I that are not shown.

Since it is desired to use the phase of respiration in the regression model, and since one cannot perform arithmetic on alphabetic symbols, one must convert the characters representing respiratory phase into a numeric form suitable for inclusion in the regression equation. The technique for doing such conversion is well-known in statistics. (See, e.g., D. C. Montgomery and E. A. Peck, *Introduction to Linear Regression Analysis*, 2nd ed., Ch. 6, John Wiley & Sons, New York, 1992, which is incorporated by reference herein). By applying such techniques, so-called "indicator functions" are obtained. In an embodiment, two indicator functions are obtained, and their values placed in matrices, called $Q_1$ and $Q_2$ herein, and are used to classify the three-way respiration phases: inspiration, expiration, and rest. Columns of the matrices $Q_1$ and $Q_2$ correspond to columns of the matrix Q, and will be referred to as the vectors $q_1$ and $q_2$, respectively.

In an embodiment of the present invention, a regression model of respiratory interference is calculated independently for each time bin for a collection of beats. Let y be the column of the filtered BSP matrix Y corresponding to some desired time bin; let $r_j$ be the corresponding column of a respiratory data matrix $R_j$; and let $q_1$ and $q_2$ be the corresponding columns of $Q_1$ and $Q_2$ containing the respiratory phase indicator function values. Then, one embodiment of the regression equation may be written as:

$$y = \sum_{j=1}^{J} (a_j r_j + c_j r_j^2) + d_1 q_1 + d_2 q_2 + k \qquad \text{Eq. 1}$$

where J represents the number of respiratory waveforms available (e.g., from two different sources); $a_j$ and $c_j$ are the weights to be determined for the respiratory data; $d_1$ and $d_2$ are weights for the respiratory phase data; and k is a constant. Since y, the filtered BSP data, contains unremoved noise that has survived the filtering steps in addition to the cardiac and respiratory effects, strict equality cannot hold in this equation. The weights and constant are determined by a regression method to find the best possible fit (according to an error metric) for the given model. After the regression fit is performed, the solution gives an estimate $\tilde{y}$, which contains the expected beat-to-beat variation (at a particular time bin) of the cardiac data due to respiratory effects, based on the regression model. The difference between the actual data in y and the estimate $\tilde{y}$ is commonly referred to as the regression residual. It will herein be referred to as the "cardiac signature" as it ideally will contain only the signature of anomalous cardiac activity. These will appear as "unexpected" beat-to-beat variations, i.e., deviations from the expected potential at a given point in the cardiac cycle that are not explained by respiratory interference. In practice, however, the cardiac signature will likely contain additional variations that are due to unremoved noise and unremoved respiratory effects.

The cardiac signature will herein be represented by the vector b:

$$b = y - \tilde{y} \qquad \text{Eq. 2}$$

Here b represents a "beat series" of cardiac data (in which beat-to-beat variations due to noise and respiratory interference have been substantially removed) containing the electrical potential of anomalous intramyocardial activity, if present.

Modeling Wenckebach Behavior Using Basis Functions

To determine the presence or absence of intramyocardial Wenckebach behavior, a set of basis functions is generated to model the different Wenckebach patterns which are to be detected. Since there are, theoretically, an infinite number of possible Wenckebach patterns, a subset of all possible patterns is chosen to represent only the most likely cases.

Figure 3A:
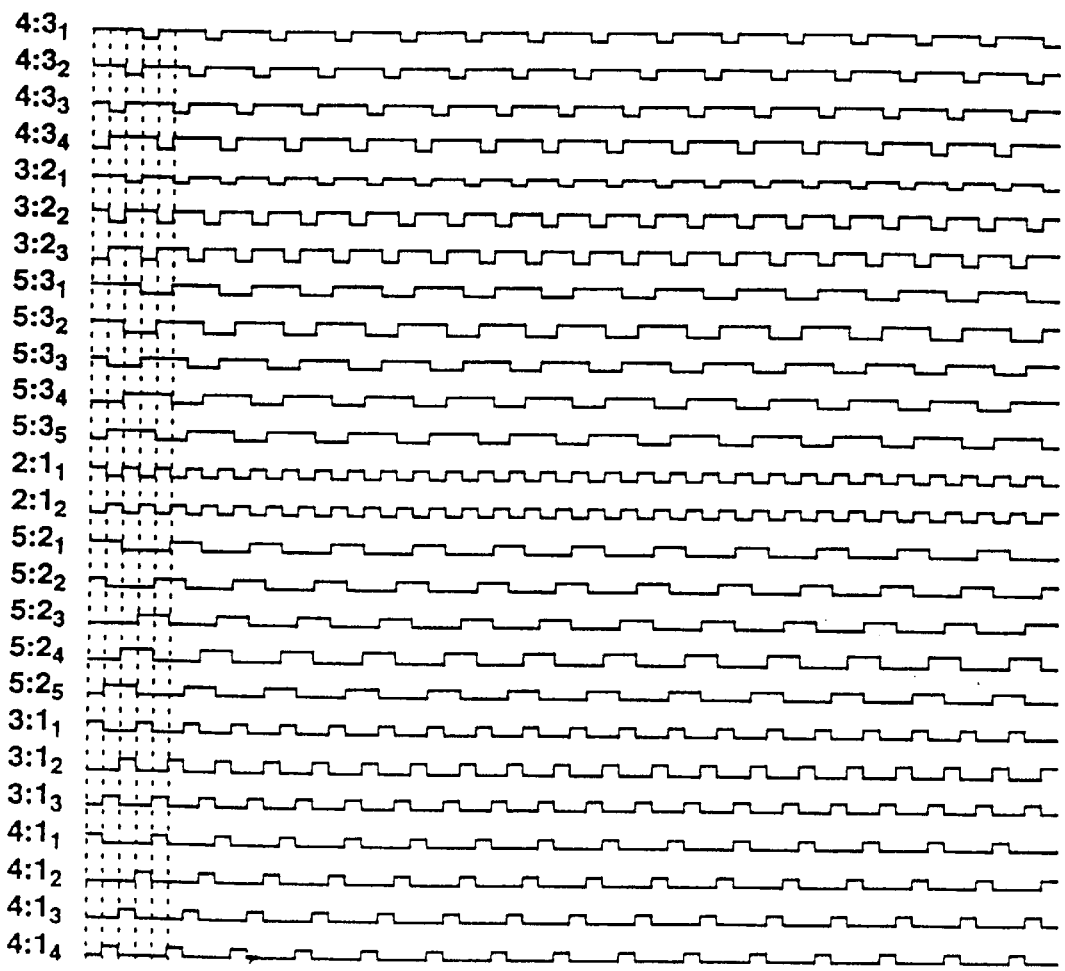
FIG. 3A shows all phases associated with seven chosen Wenckebach modes; in this example, 26 Wenckebach patterns are shown over 60 beats.

For illustration, FIG. 3A shows a chosen set of Wenckebach patterns over 60 beats, depicted in a graphical manner. This illustration contains seven M:N Wenckebach patterns that are believed the most likely to be encountered: 4:3,3:2, 5:3, 2:1, 5:2, 3:1, and 4:1. These patterns will be referred to as the Wenckebach "modes." The modes appear in the diagram in order of decreasing activation ratio (0.75, 0.67, 0.60, 0.50, 0.40, 0.33, and 0.25). Since a particular Wenckebach mode can begin at any beat, each M:N mode has M associated "phases," which represent the M possible start times for a mode having a period of M beats. Subscripts are used to specify the particular phase of a given mode. All phases of a particular mode must be included in a set of Wenckebach basis functions since the phase of a Wenckebach mode cannot be known a-priori. In addition, one must account for the possibility of multiple phases of a given mode being present simultaneously, each generated by different regions of the heart. Thus, to represent all the phases of the seven modes, 26 basis functions are required.

In FIG. 3A, the dashed vertical lines on the left side delimit the occurrence of beats, and are shown only for the first through the fifth beats. For each plot, a high value represents myocardial tissue that responds to a stimulus for a beat, whereas a low value represents the failure of the tissue to respond. For example, the top tracing shows the $4:3_1$, pattern (4:3 mode in phase 1), which consists of repeating cycles of three responses followed by a failure. The second tracing shows the $4:32_2$ pattern (4:3 mode in phase 2), similar to $4:31_1$ but shifted earlier by one beat so that the failed response occurs on the third beat instead of the fourth, i.e., repeating cycles of respond, respond, fail, respond. The other tracings of Wenckebach patterns may be similarly interpreted.

In order to detect Wenckebach patterns in the cardiac signature data, a solution is computed which represents the best fit of a linear combination of the basis functions to the cardiac signature. To perform this calculation, the basis functions (e.g., those depicted in FIG. 3A or a subset) are converted to a mathematical representation in a matrix. Using a value of 1 to represent a response during a beat, and a value of 0 to represent a failure to respond during a beat, each basis function is converted into a vector containing 1's and 0's. These vectors are placed side-by-side into the columns of a $\{n_b \times n_W\}$ matrix $\tilde{W}$, where $n_b$ is the number of rows and corresponds to the number of beats to be examined, and $n_W$ is the number of columns and corresponds to the number of Wenckebach basis functions (including all phases of the chosen modes). Any matrix so containing a set of Wenckebach basis functions will herein be referred to as a "Wenckebach matrix." As an example, an eight-beat by 26-pattern Wenckebach matrix $\tilde{W}$ looks like the following:

$$\tilde{W} = \begin{bmatrix} 11101101110010110001001000 \\ 11011011100101100010010001 \\ 10110111001110000110100010 \\ 01111100011101001101000100 \\ 11101010111010011000011000 \\ 11010111110001110000100001 \\ 10111101100110100011000010 \\ 01111011001101000110011100 \end{bmatrix}$$

Finding a Unique Solution

As previously stated, Wenckebach activity is detected by fitting the cardiac signature data with a linear combination of a set of basis functions. From the weights given by the solution, one can infer whether or not Wenckebach activity is present, and if so, the strength of the Wenckebach pattern (or patterns if more than one is present).

Given a $\{n_b \times r_W\}$ Wenckebach matrix $\tilde{W}$ (the $n_W$ columns of which comprise a set of Wenckebach basis functions), and a cardiac signature vector b of length nb (containing a beat series of filtered BSP data for a given time bin after QRS onset for nb beats, which beat series has had the respiratory interference removed by regression), the relationship between them can be written as:

$$\tilde{W}x = b \qquad \text{Eq.3}$$

where x is a vector of $n_W$ weights to be determined. Once a solution is found, each element of the vector x will represent the strength of the corresponding Wenckebach basis function.

The solution to Eq. 3 can be found by a variety of methods. Once again, regression methods may be employed to find the best fit. One may use a least squares or a robust method (e.g., least-one-norm: see, e.g., Bloomfield and W. L. Steiger, *Least Absolute Deviations*, Boston: Birkhäuser, 1983). If one makes the assumption that the noise subspace (which includes respiratory interference) is orthogonal to the Wenckebach signal subspace, the least squares solution is given by:

$$x = \tilde{W}^I b \qquad \text{Eq. 4}$$

where $\tilde{W}$ is a generalized inverse of $\tilde{W}$ (see S. S. Haykin, Adaptive Filter Theory, Englewood Cliffs: Prentice Hall, 1991, pp. 409–411, for the Penrose-Moore generalized inverse).

However, there is a problem with computing the generalized inverse of $\tilde{W}$ in that the matrix $\tilde{W}$ is singular, and hence the generalized inverse does not exist. That the matrix is singular can be seen by noting that the basis functions for all phases of a Wenckebach mode sum to a constant-valued vector. For example, the first four basis functions in FIG. 3A (representing all phases of the 4:3 mode) sum to a vector containing the value three in each element. This linear dependence makes the matrix singular. FIG. 3A also reveals that for each pattern in the top half of the figure, a pattern in the lower half exists such that their sum is equal to a vector containing all ones, also indicating singularity of the matrix containing this set of basis functions. Even if a method other than least squares is used to solve Eq.3, the singularity of $\tilde{W}$ implies that a unique solution cannot be found.

Figure 3B:
FIG. 3B shows the basis fiinctions associated with the Wenckebach patterns of FIG. 3A after orthogonalization by the SVD method.
Figure 3B:
Figure 3B:
Figure 3B:
Figure 3B:

To detect the presence of Wenckebach activity by solving Eq. 3, a non-singular matrix is needed. The Gram-Schmidt orthogonalization procedure allows this to be achieved. However, the numerical stability of the original Gram-Schmidt procedure is quite poor. Consequently, singular value decomposition (SVD) is used to orthogonalize the singular Wenckebach matrix $\tilde{W}$ (see W. H. Press et al., supra, incorporated by reference herein). When SVD is used to orthogonalize the matrix $\tilde{W}$ containing the 26 basis functions graphically depicted in FIG. 3A, one obtains 26 new basis functions, each having a corresponding singular value. In this case, the singular values for the new basis functions 11 through 26 are zero, indicating the very extensive singularity of the original Wenckebach matrix; in addition, this indicates that the new basis functions 11 through 26 are not needed. Thus, FIG. 3B shows a graphical representation of the meaningful basis functions 1 through 10 that correspond to non-zero singular values. The label shown above each function is its period, which is the number of beats until the pattern repeats. In FIG. 3B, one basis function is constant, one basis function has a period of two, two basis functions have a period of three, two basis functions have a period of four, and four basis functions have a period of five. It can be said that these ten basis functions completely "span" the modeled Wenckebach space, in that an appropriate linear combination of them can synthesize each of the original 26 Wenckebach patterns. For example, a weighted sum (using positive and/or negative weights) of the first (constant) and second (period 2) basis functions yields either phase of the 2:1 mode. Similarly, a weighted sum of the functions having period three and the constant function can represent any phase of the 3:2 or 3:1 modes, etc.

The new set of orthogonalized basis functions, derived from the singular Wenckebach matrix $\tilde{W}$, are placed in the columns of a matrix W. For the sake of clarity, W will be used hereinafter to represent an orthogonalized, nonsingular Wenckebach matrix. Given a $\{n_b \times n_W\}$ Wenckebach matrix $\tilde{W}$ (which $n_W$ columns comprise a set of orthogonal Wenckebach basis functions, here the $n_w$ will be smaller than the $n_w$ of $\tilde{W}$), and a cardiac signature vector b of length $n_b$, we can re-write Eq. 3 using W as follows:

$$W x = b \qquad \text{Eq. 5}$$

where x is a vector of weights to be determined, having length $n_W$ corresponding to the reduced number of orthogonal basis functions. A least squares solution to Eq. 5 is given by:

$$x = W^I b \qquad \text{Eq.6}$$

where $W^I$ is the generalized inverse of W, and can now be computed since W is nonsingular.

Each element in the vector x (given by a solution to Eq. 5) is a weight for the corresponding orthogonal basis function and represents the strength of the basis function in the cardiac signature. However, the value of the weight no longer can be used to determine the strength of a specific phase of a Wenckebach mode, since a basis function in the orthogonal set no longer individually represents a particular Wenckebach pattern. The weights corresponding to all basis functions of a given period, however, can be used to determine the strength of any mode having that period. For example, the weights corresponding to basis functions having period three can be used to determine whether any 3:N (i.e., 3:2 or 3:1) Wenckebach activity is present, but cannot uniquely identify either the 3:2 or 3:1 mode, nor any of their particular phases. For this reason, the nonsingular matrix W is referred to as "probe matrix" herein as it allows for the detection of the presence of Wenckebach activity. The estimation of the strength of an individual phase can follow once Wenckebach activity of a given period has been detected. However, specification of precisely which modes are present requires independent knowledge as to the anatomic site likely to be experiencing the Wenckebach activity.

Detection of Wenckebach Activity

As described above, a (linearly dependent) set of Wenckebach patterns (representing modes and phases) to be evaluated is placed in the columns of a Wenckebach matrix $\tilde{W}$, forming a set of basis functions. This matrix is then orthogonalized to remove singularity, forming a nonsingular Wenckebach matrix W. Given a cardiac signature vector b, one can then solve Eq. 5 to find x, which is the vector of Wenckebach strengths.

To ensure that the vector x will not falsely indicate the presence and amplitude of Wenckebach activity when the cardiac signature vector b has a significant noise component, a detection statistic is computed. Ideally, a matched filter would be used for this purpose, see L. L. Scharf, *Statistical Signal Processing: Detection, Estimation, and Time Series Analysis*, Addison-Wesley Co., Reading, Mass., 1991. However, such a filter requires the knowledge of both the signal and the standard deviation of the noise. In the present case, neither the composition of the signal nor the noise statistics are known. Thus, in the present invention, a constant false alarm rate (CFAR) matched subspace filter is used. This filter produces a generalized likelihood ratio (GLR) detection statistic, which allows one to judge the significance of any Wenckebach power in x.

Given a model of possible Wenckebach activity, defined by the set of basis functions in W, the CFAR GLR statistic F is proportional to a ratio, the "GLR," which is the "energy" in the cardiac signature that is accounted for by the model divided by the energy that is not accounted for by the model:

$$GLR = \frac{\text{power in } b \text{ accounted for by model}}{\text{power in } b \text{ not accounted for by model}} \qquad \text{Eq. 7}$$

The difference between F and GLR is a constant proportionality factor (i.e., F is proportional to GLR), which is related to the degrees of freedom (in other words, the dimensions of matrix W). This difference is clear to one skilled in the art (see L. L. Scharf, p. 148, supra). The GLR may be "loosely" interpreted as a Signal-to-Noise ratio, as it gives larger values when there is obvious Wenckebach activity and little noise, and gives smaller values when there are large amounts of noise and/or interference still present.

The denominator, i.e., the power in b not accounted for by the model, can be computed by subtracting the power in b accounted for by the model from the total power in b. This gives:

$$GLR = \frac{\text{power in } b \text{ accounted for by the model}}{\text{total power in } b - \text{power in } b \text{ accounted for by the model}} \qquad \text{Eq. 8}$$

Since x represents the strength of the basis functions in b, W x gives the best estimate of b in terms of the modeled basis functions (i.e., the components in b accounted for by the model). The estimate of b is $$\hat{b} = Wx$$

The power in b accounted for by the model is thus $\hat{b}^T \hat{b}$ (where $\hat{b}^T$ is the transpose of $\hat{b}$), i.e., the sum of the squares of the values in $\hat{b}$. The total power in b is simply given by $b^T b$. Substituting the mathematical terms into Eq. 8:

$$GLR = \frac{\hat{b}^T \hat{b}}{b^T b - \hat{b}^T \hat{b}} \qquad \text{Eq. 9}$$

If the GLR exceeds a threshold, determined by sensitivity/specificity considerations, then Wenckebach activity is declared to have been detected. The threshold can be set by trying various levels and examining the error rates for a teaching data set; this can be done by one skilled in the art. Since a GLR is computed for each time bin, differing threshold levels are found for different time bins because the interference and noise characteristics are different across the QRST complex. In one embodiment of this invention, the time bins are divided into 5 regions: QRS, S-T region, first third of T-wave, second third of T-wave, and last third of T-wave. A different GLR threshold is used for the time bins that fall into these regions.

The GLR computed in Eq. 9 represents the likelihood that "any" Wenckebach mode modeled by W is present. Therefore, the GLR of Eq. 9 is referred to as the "overall" GLR herein. However, using a similar technique, one can compute an individual GLR for each family of modes having the same periodicity (e.g., all 3:N modes, including 3:1 and 3:2). Referring FIG. 3B, it is noted that each new basis function in the nonsingular Wenckebach matrix W has an associated periodicity. W can be partitioned (by columns) into sub-matrices that correspond to these periods:

$$W = [W_c \ W_2 \ W_3 \ W_4 \ W_5]$$

where $W_c$ is the constant basis function, and $W_m$ are matrices containing basis functions of period m. One can similarly partition the mode strength vector x into corresponding groups of elements:

$$X = [X_c \ X_2 \ X_3 \ X_4 \ X_5]$$

where $x_c$ is the weight given to the constant basis function, and $x_m$ are the weights for basis functions of period m.

Then, the components in b accounted for by the basis functions $W_m$ (having period m) are given by:

$\hat{b}_m = W_m x_m$ and the corresponding power is given by $\hat{b}^T_m \hat{b}_m$. The reduced-model GLR is then given by:

$$GLR_m = \frac{\hat{b}^T_m \hat{b}_m}{b^T b - \hat{b}^T_m \hat{b}_m} \qquad \text{Eq. 10}$$

where $GLR_m$ represents the likelihood that Wenckebach activity with a period m is present. Detection thresholds may also be found for each $GLR_m$.

Estimating the Strength of Wenckebach Activity

Once Wenckebach activity has been detected by a GLR exceeding a threshold, the strength of the Wenckebach activity can be estimated. The overall power (i.e., for all modeled modes) of the Wenckebach activity is given by the power in the mode strength vector, x: $x^T x$ (i.e., the sum of the squares of the weights in x). The root-mean-squared (RMS) voltage is the square root of the power, and will be directly proportional to the voltage of the Wenckebach activity in the raw BSP.

The power of a set of modes with a given periodicity can similarly be computed by using the corresponding sub-vectors of the partitioned mode strength vector, x, the partitioning done as in the previous section. For example, the power of the Wenckebach modes with period m is given by $x^T_m x_m$. The RMS voltage is also calculated by taking the square root of the power.

Discarding Outlying Data to Improve Wenckebach Detection And Estimation

Often one or more beats in a set of beats being analyzed for Wenckebach activity will be highly anomalous in some fashion, in a way not related to Wenckebach behavior. For example, a beat may be extremely noisy due to a burst of EMI or muscle tremor; or it may be overly distorted by an anomalously deep breath. It will be advantageous to discard such outlying beats so that Wenckebach activity may be more readily detected.

Various techniques for removing abnormal beats are known in the art and can be adapted to the present invention. For example, template matching on beats detected in the BSP may be used to detect beats having extremely anomalous morphology (i.e., shape). Algorithms may be used to detect anomalous breaths, and the beats occurring during such breaths may be discarded.

Other methods may be employed on the beat series of time bin values, to detect an outlying value of an individual time bin average. One technique suitable to adjusting for such outlying values are the alpha-trimming methods. One such method has been applied to trimming outlying values of BSP data (see U.S. Pat. No. 5,613,496, which is incorporated by reference herein). Extensions of these techniques, which are applicable especially when the amount of data to be examined is limited, are the adaptive alpha trimming methods, which make decisions on the amount of outlying data to trim based on the aggregation of the data points. Special methods have been developed for the context of regression. (On adaptive trimming techniques, see e.g., R. V. Hogg et al., "On Adaptive Estimation," *J Stat. Planning and Inference*, 9:333–343, 1984, which is incorporated by reference herein. Parallel methods devised for regression are also germane.)

One advantage of the time-domain based approach of the present invention over prior art frequency—domain methods for detection of anomalous myocardial activity is that the present technique readily handles the discarding of outlying beats or portions of beats. Frequency domain techniques have difficulty in this regard. In the present invention, once a set of outlying beats has been identified which is to be discarded, the data values are removed from the beat series vector y; from the respiratory series r; and the corresponding rows from the Wenckebach matrix W are discarded. The Wenckebach detection method may then proceed as usual, using the smaller vectors and matrix. By removing a beat from the beat series data y, one has "interrupted" any Wenckebach patterns that may be present. However, by similarly interrupting the Wenckebach patterns in the basis function matrix, the remaining portions of the basis functions will remain aligned with any Wenckebach activity that is present.

Testing for Respiratory Interference That May Mask Wenckebach Activity

Although regression is used to significantly reduce the effects of respiration in the BSP, it is likely that some respiratory effects will remain in the cardiac signature data. Fortunately, heart rate and respiratory rate usually behave as if generated by independent oscillators—they usually do not synchronize into an integral multiple of each other, but most often tend to drift in and out of phase with respect to one another. Thus, the respiratory effects usually do not consistently interfere with the Wenckebach pattern, and the pattern can still be detected in the cardiac signature. However, heart rate and respiration will occasionally synchronize into integral multiples of each other, for example, at ratios of 4:1 or 3:1. When this occurs, the remaining respiratory effects may falsely be detected as Wenckebach activity at the corresponding period (i.e., with period 4 or 3). A test to determine when such respiratory interference may masquerade as Wenckebach activity is desirable.

To detect when synchronous respiratory influences may masquerade as Wenckebach activity, one looks for the presence of Wenckebach power in the respiratory signal itself. To do this, one uses the respiratory beat series r, which is the vector of beat-to-beat values of the respiratory waveform sampled at a time corresponding to that of each BSP time bin (as shown in FIG. 2B). One then looks for the strength of each Wenckebach mode in this series by solving the equation:

$$W x = r \qquad \text{Eq. 11}$$

which is similar to Eq. 5, only here the cardiac signature vector b is replaced by the respiratory series r.

In a manner similar to detection of Wenckebach activity in the cardiac signature, one solves this equation (using the generalized inverse of W, if desired), and then similarly computes the GLR's. If the GLR is significant for the Wenckebach modes of a given period, this indicates that respiratory variations are occurring in a manner corresponding to that set of Wenckebach patterns. In this case, one may wish to ignore (or examine more closely) a detection of these modes of Wenckebach activity that may have occurred with this particular series of beats.

The above test for possible respiratory interference may be performed on either one, or on all respiratory waveforms if more than one is available.

Summary of Steps

The following is a summary of the steps of an embodiment of the method of the present invention to estimate the presence or absence of the intramyocardial anomalous activity.

1. Choose a set of Wenckebach patterns to be detected; create basis function matrix, $\tilde{W}$.
2. Use SVD on $\tilde{W}$ to create a nonsingular Wenckebach matrix, W.
3. Acquire BSP and respiration signals.
4. Detect beat locations.
5. Filter BSP to remove EMI and baseline wander.
6. Identify beat on sets.
7. Average adjacent samples into time bins across the beat.
8. Discard outlying beats (noisy or during anomalous breaths), and corresponding rows from the Wenckebach matrix W. For each time bin the following is performed:
9. Discard outlying values in the beat series of time bin averages, and the corresponding rows of the Wenckebach matrix W.
10. Use regression to model the respiratory interference in the filtered BSP.
11. Compute the cardiac signature vector b by subtracting the modeled filtered BSP from the actual filtered BSP.
12. Solve Wx=b for the Wenckebach mode strength vector, x. (The generalized inverse of W may be used).
13. Compute the generalized likelihood ratio (GLR) detection statistics for overall and/or individual periods of Wenckebach activity and compare to a threshold.
14. Given detection of Wenckebach activity, compute the RMS voltages of the activity.
15. Test for the possibility of respiratory interference masquerading as Wenckebach activity with a particular period by computing the mode strength and GLR's of Wenckebach activity in the respiration signal(s). If above a threshold, ignore (or examine closely) detections of Wenckebach activity with the same period.

EXAMPLE

Figure 4:
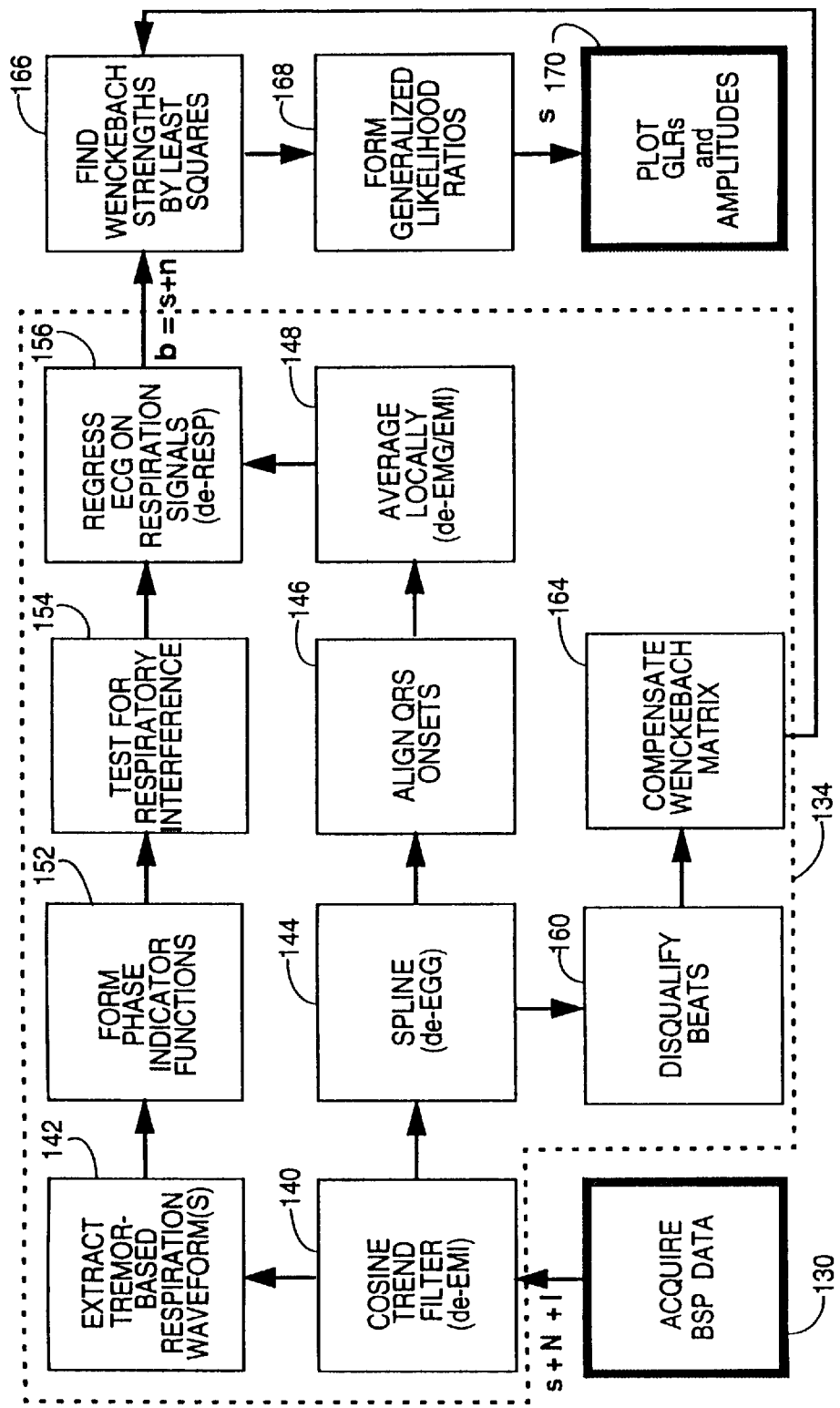
FIG. 4 shows an embodiment of a process for determining whether Wenckebach activity is present according to the present invention.

This example illustrates how the technique can be applied. FIG. 4 shows the flow diagram of the procedure used in this example, which is used for illustrative purposes only. In this example, BSP signals are obtained from leads connected to a patient's body (step 130). The BSP data can be represented by (s+N+I) where s is the Wenckebach signal, N is the total noise not including respiratory noise, and I is the respiratory interference. The BSP data are processed to obtain cardiac signature data substantially without the respiratory interference I (dotted block 134). The BSP data are filtered by the cosine trend filter (also called sinusoidal trend filter, see above) to remove noise from electromagnetic interference (EMI), (step 140), i.e., to "de-EMI" the data. On one branch the EMI-filtered BSP data are processed to extract a respiration waveform by analyzing the muscle tremor (step 142), see, e.g., U.S. patent application Ser. No. 08/769,557, docket number 10960801-1, supra. On the other branch, a cubic spline method is used on the EMI-filtered BSP data to remove baseline wander noise due to electrode artifact and electrogastric (EGG) sources, i.e., to de-EGG (step 144). Heart beats in the EMI- and EGG-filtered BSP data are detected and aligned so that the QRS onset times are coincident (step 146) and then short-term-averaged into time bin values to reduce muscle tremor noise (i.e., "de-EMG") and remaining EMI. This is achieved by averaging together sets of a small number of adjacent data points (e.g., 10 data points of data sampled at 2,000 samples per second) to obtain local averages spanning 5 millisecond wide time bins starting at the onset point (step 148).

As an option, in this example, the respiratory waveform is analyzed to obtain phase indicator functions (step 152), which can be included in the equation for estimating (modeling) the respiratory interference on the BSP (see Eq. 1). Also, a check for Wenckebach characteristics in the respiratory waveform is performed to determine if respiratory interference may falsely appear as intramyocardial Wenckebach behavior in the cardiac data (step 154). If the respiratory waveform has insignificant Wenckebach characteristics, then the filtered BSP data are regressed on the respiratory data to obtain the modeled respiratory interference. The difference between the actual filtered BSP and that predicted by the respiratory interference model is an extracted cardiac signature vector, b, consisting of any true Wenckebach signal s and unremoved noise n (step 156).

The filtered BSP data are also checked to find beats that are anomalous, e.g., those with outlying values far from neighboring data points, or excessively noisy (step 160). Standard statistical methods can be used to find such beats. Such disqualified beats are discarded. With some beats being discarded, the rows corresponding to the disqualified beats in the Wenckebach matrix are also removed (step 164).

The Wenckebach mode strengths x are computed by solving for the best solution to the equation: Wx=b. Using a least squares solution, b is multiplied by the generalized inverse of the Wenckebach matrix (step 166). By analyzing the power of the extracted Wenckebach signal relative to that of the residual noise by computing a generalized likelihood ratio (GLR), the likelihood of the extracted Wenckebach signal representing true Wenckebach activity is assessed (step 168). The GLR's and the Wenckebach strengths can be displayed, e.g., plotted on paper to show the GLR's for each time bin and Wenckebach period, and the estimated RMS amplitude of the Wenckebach activity (step 170).

Figure 5:
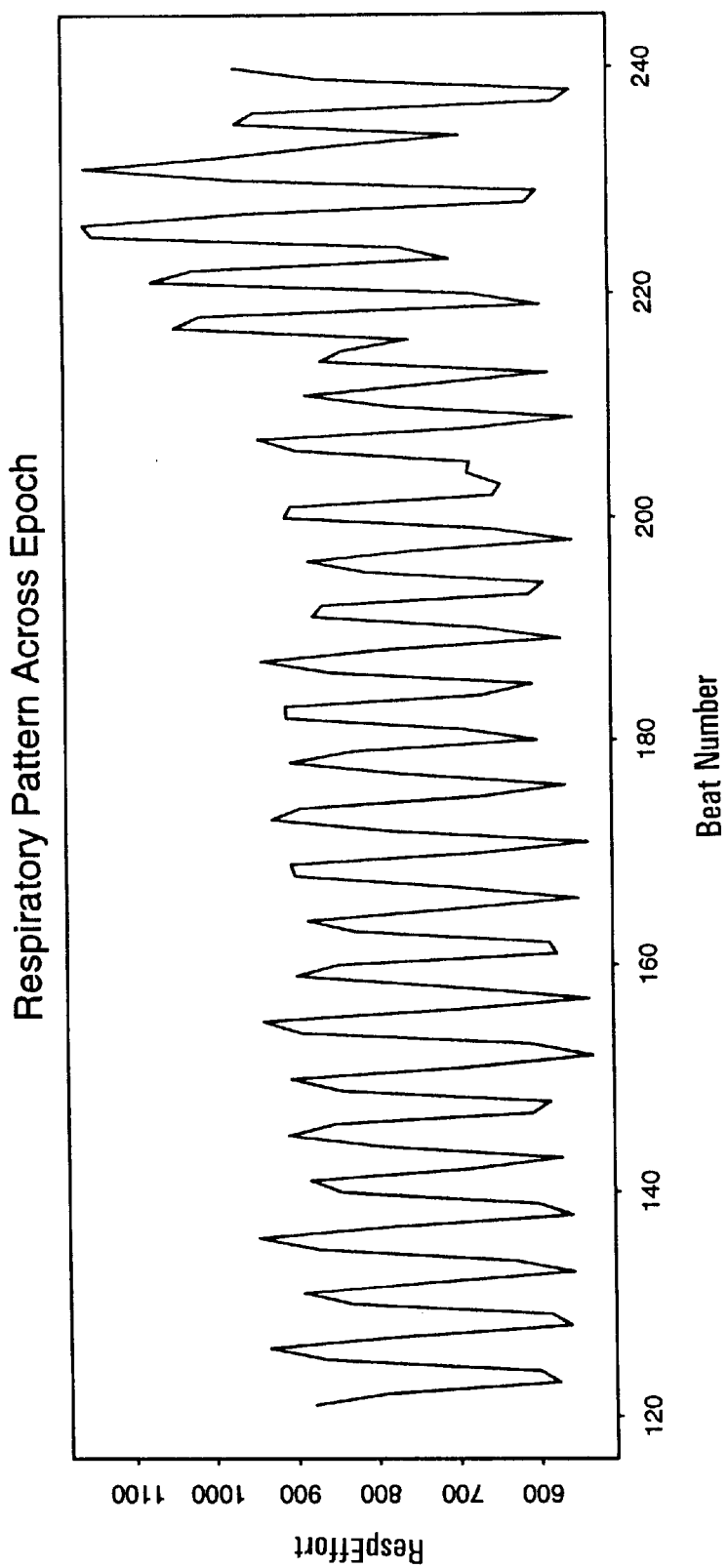
FIG. 5 shows an example waveform of respiratory data sampled once per beat for a human subject; beats 121 through 240 from a dataset are shown in this example.
Figure 6:
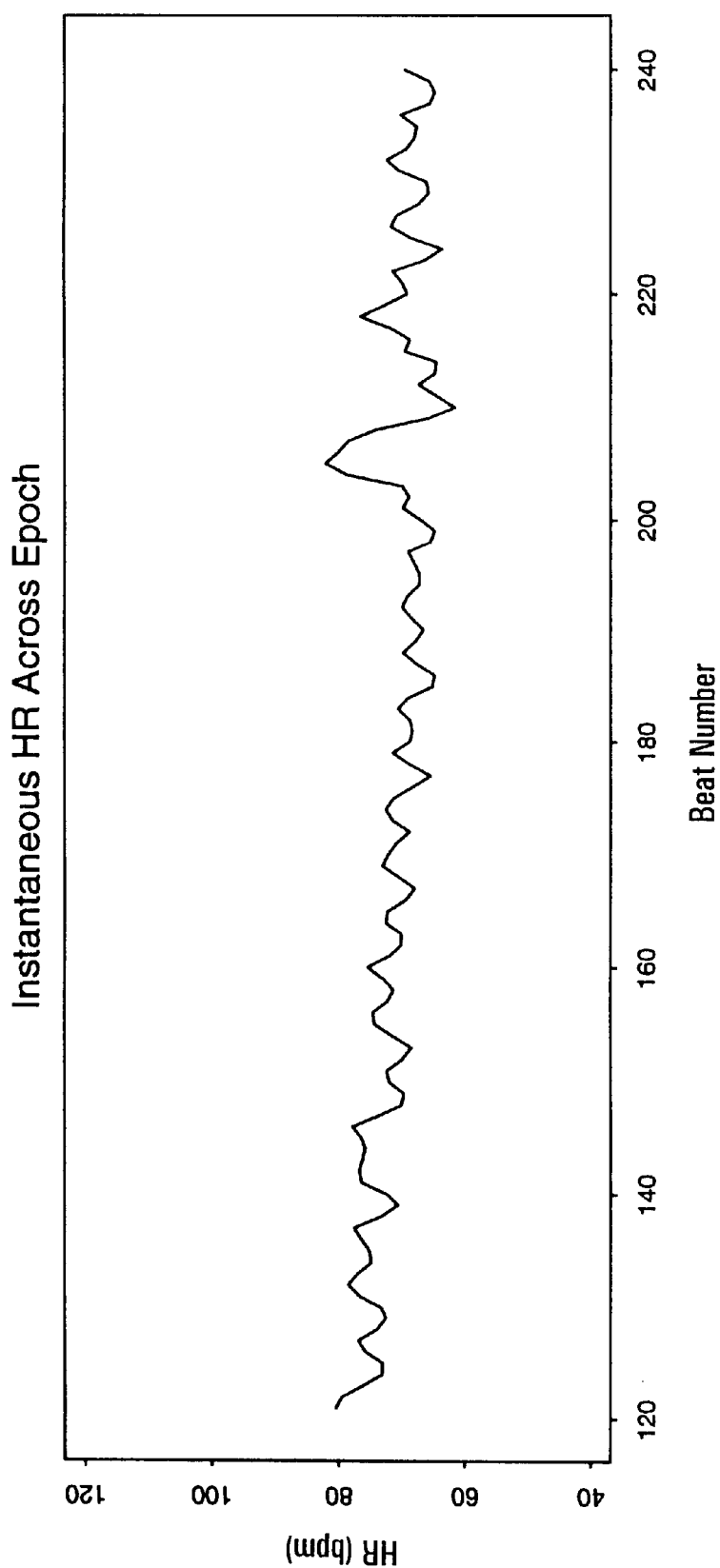
FIG. 6 shows a waveform of instantaneous heart rate in the illustrative run of FIG. 5.

For illustration, FIGS. 5 to 12 show data reflecting the detection of simulated Wenckebach activity in a person. BSP were measured from the body surface of the person as conventionally done for traditionally called "electrocardiogram (ECG)" recording using quasi-orthogonal leads. In the BSP data measured from the body, a 5 microvolts RMS voltage corresponding to a Wenckebach 3:2 (phase 1) pattern was added to the BSP signals of the person (who was a healthy person) to simulate the presence of Wenckebach electrical activity in the signal. The simulated Wenckebach pattern was added to each entire QRST complex, from onset to 500 milliseconds after onset. FIG. 5 shows a respiratory waveform from the person sampled at the times corresponding to each beat onset for an interval containing 120 beats (i.e., beats 121 through 240). Such an interval of beats is hereinafter called an "epoch" of data. The respiratory data of FIG. 5 were obtained by extracting muscle tremor from BSP signals using the technique of U.S. application Ser. No. 08/769,557, supra. FIG. 6 shows the heart rate during this epoch. It is noted that the instantaneous heart rate varied from about 60 to 80 beats per minute.

Figure 7:
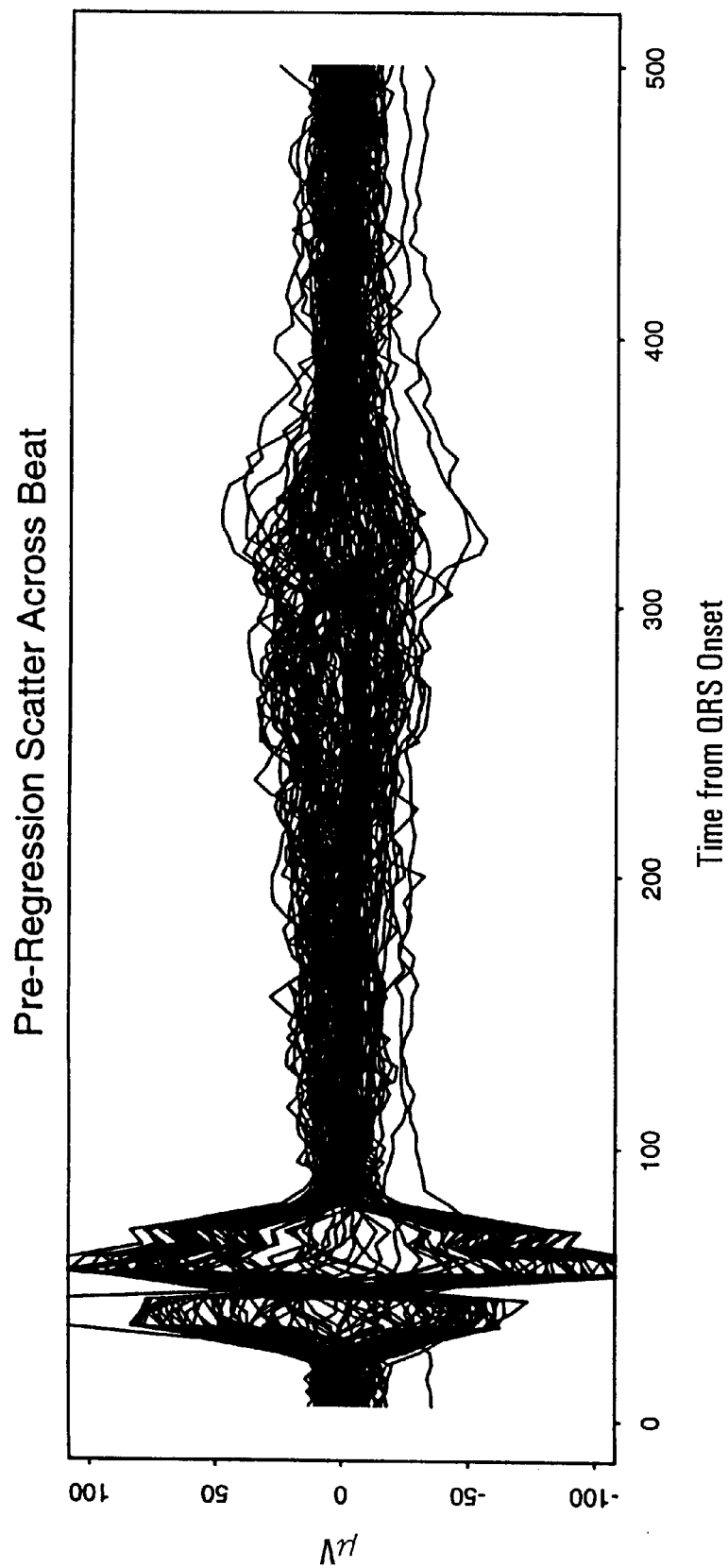
FIG. 7 shows the pre-regression scattering of filtered, time-bin-averaged, zero-mean, BSP data for beats that have been aligned according to their onsets of the illustrative run of FIG. 5.
Figure 8:
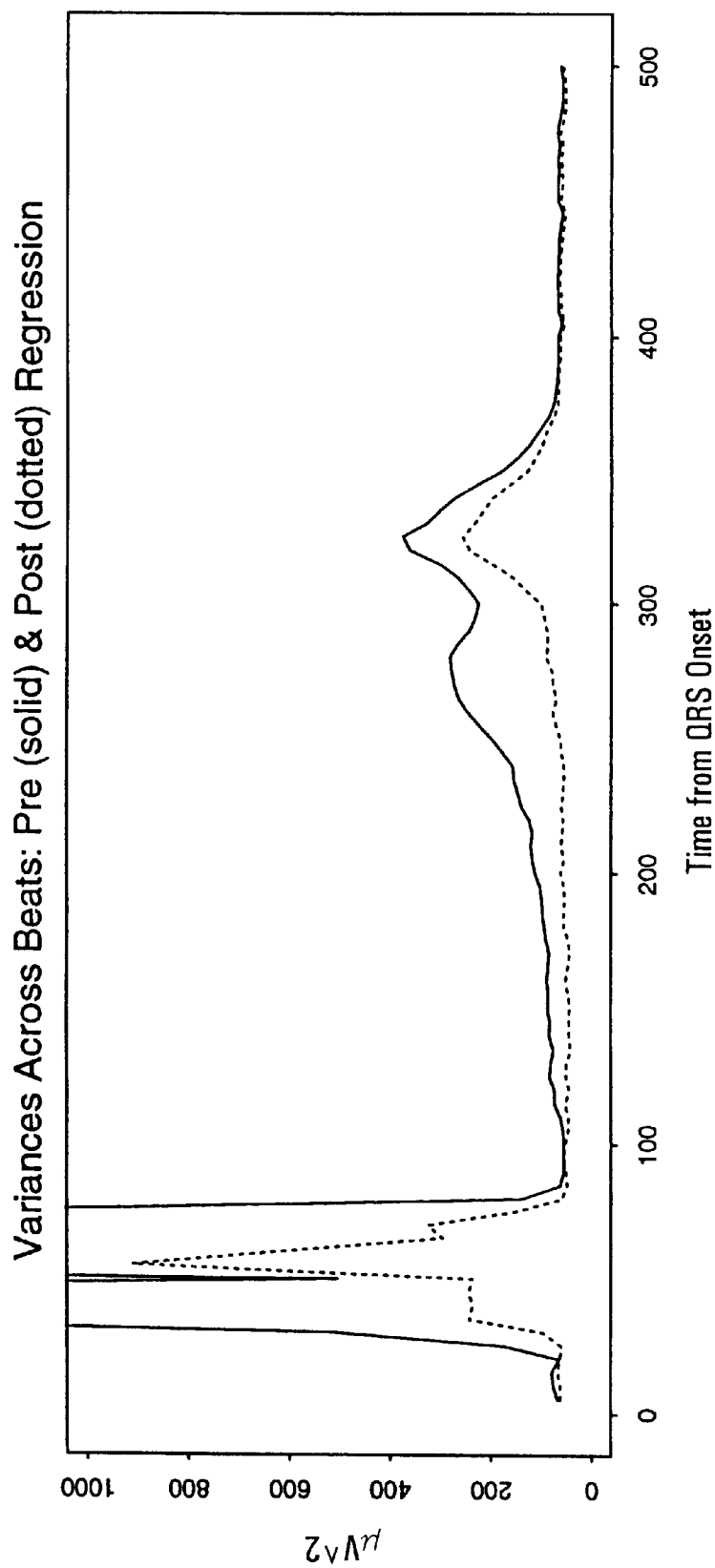
FIG. 8 shows the variances of the filtered BSP of the zero-mean time bins, comparing the pre-regression variances to the post-regression variances of the illustrative run of FIG. 5.

FIG. 7 shows the variations in the filtered BSP data for each beat in the epoch after being aligned according to the beat onset times and averaged into 5 millisecond wide time bins. The mean value at each time bin has been subtracted to remove the regular repeating electrical cardiac voltage of the QRST complex, so that only the variations from the mean can be seen. FIG. 8 shows the variance at each time bin of the plotted zero-mean beats in FIG. 7 before regression to remove respiration effects (solid curve) and after the respiratory component of the variation is removed (dotted curve). The variance is much less during the QRS and T-waves, showing the effectiveness of the regression technique in removing the beat-to-beat respiratory variation.

Figure 9:
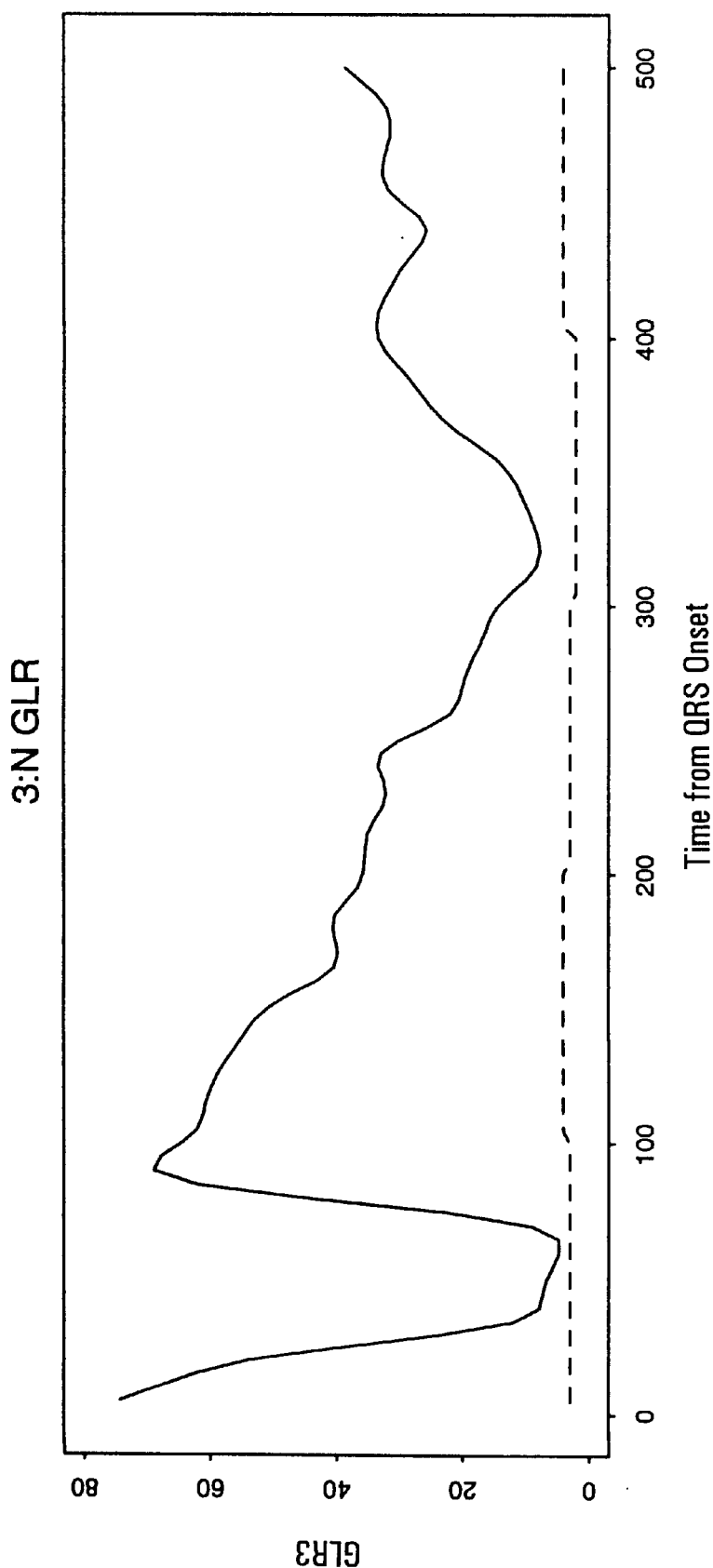
FIG. 9 shows the generalized likelihood ratio (GLR) values for the 3:N (period 3) mode of the illustrative run of FIG. 5; a simulated 5 microvolts RMS 3:2 Wenckebach pattern has been added to the BSP data.
Figure 10:
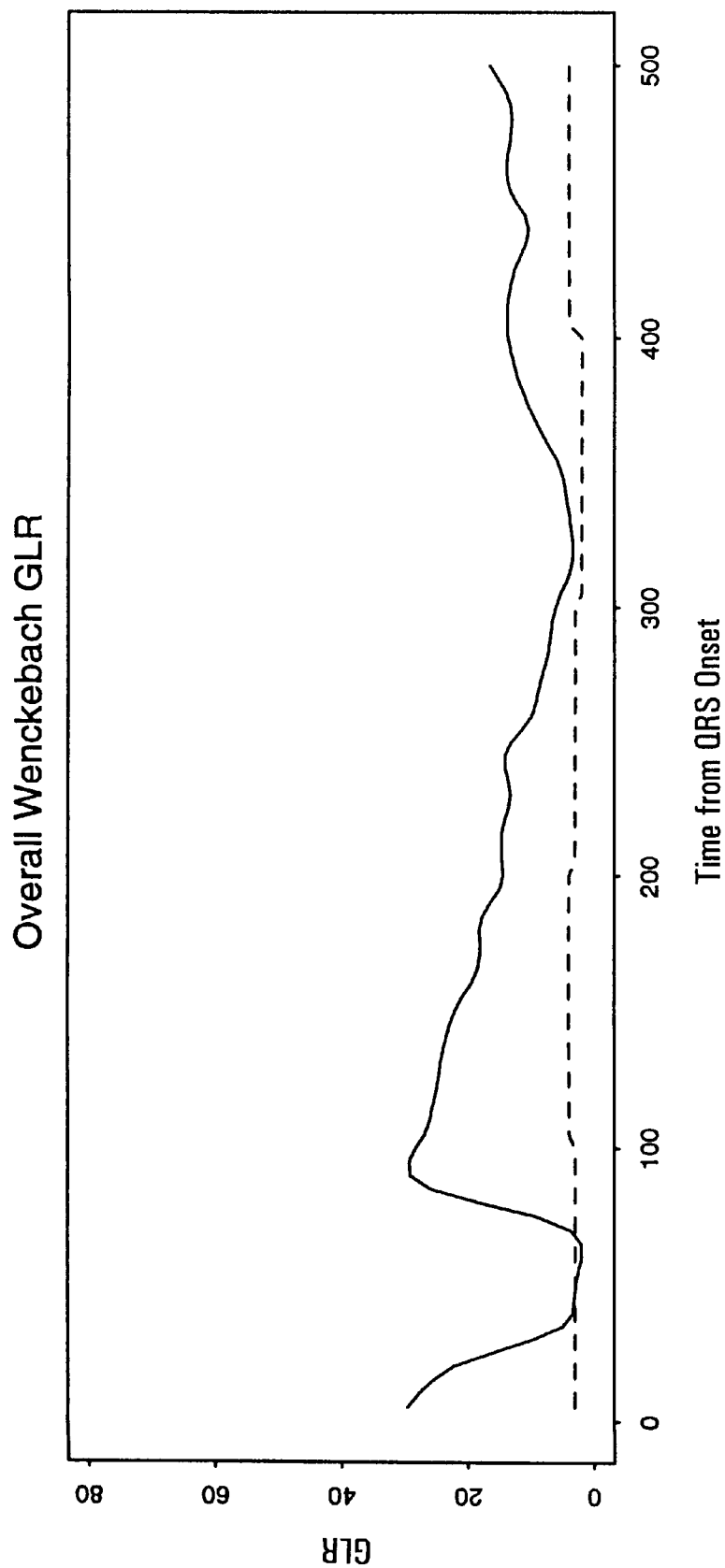
FIG. 10 shows the overall GLR values for all modeled modes of the illustrative run of FIG. 5; a simulated 5 microvolts RMS 3:2 Wenckebach pattern has been added to the BSP data.

After calculating the values of the cardiac signature vector b and solving for the mode strength vector x, the generalized likelihood ratios (GLRs) are computed. This is done for each time bin from onset to 500 msec. after onset. A plot of the GLR values for the 3:N modes (modes having period 3) and for all modes ("overall") are shown in FIGS. 9 and 10, respectively. Linear thresholds are shown as the dotted lines towards the bottom of each plot. The GLRs indicates that the power due to Wenckebach signals was significantly bigger than that of noise for most of the QRST complex. The fact that all the 3:N GLR values exceed the threshold indicates the presence of substantial Wenckebach activity having a period 3 (FIG. 9). The overall GLR values (FIG. 10) also show a high likelihood of Wenckebach activity in all regions except for a small region during the QRS complex where the GLR drops slightly below the threshold. Small GLRs for the Wenckebach modes of 2:1 and 4:N (not shown in graphs) indicate that no significant power in these modes is present.

Figure 11:
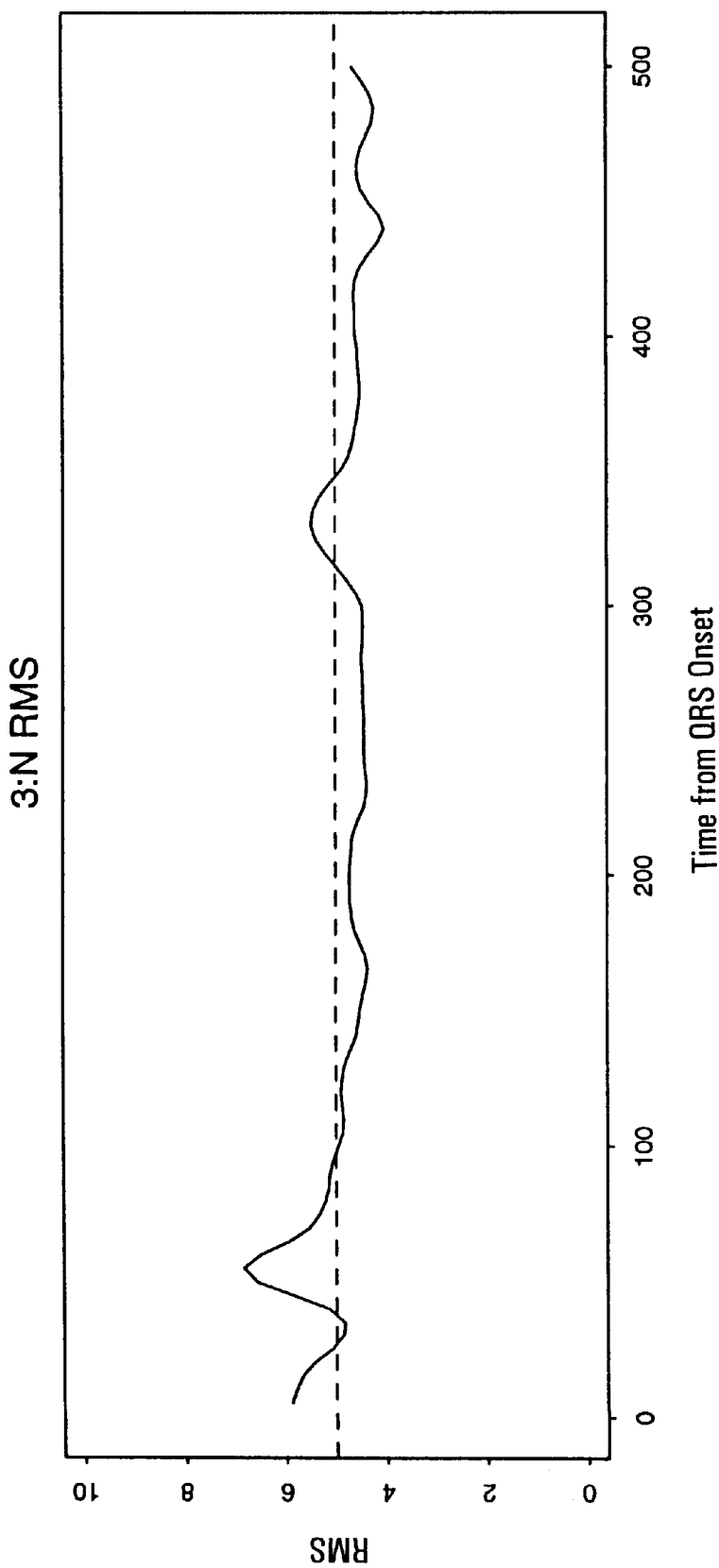
FIG. 11 shows the estimated RMS amplitude of the 3:N mode of the illustrative run of FIG. 5; a simulated 5 microvolts RMS 3:2 Wenckebach pattern has been added to the BSP data.
Figure 12:
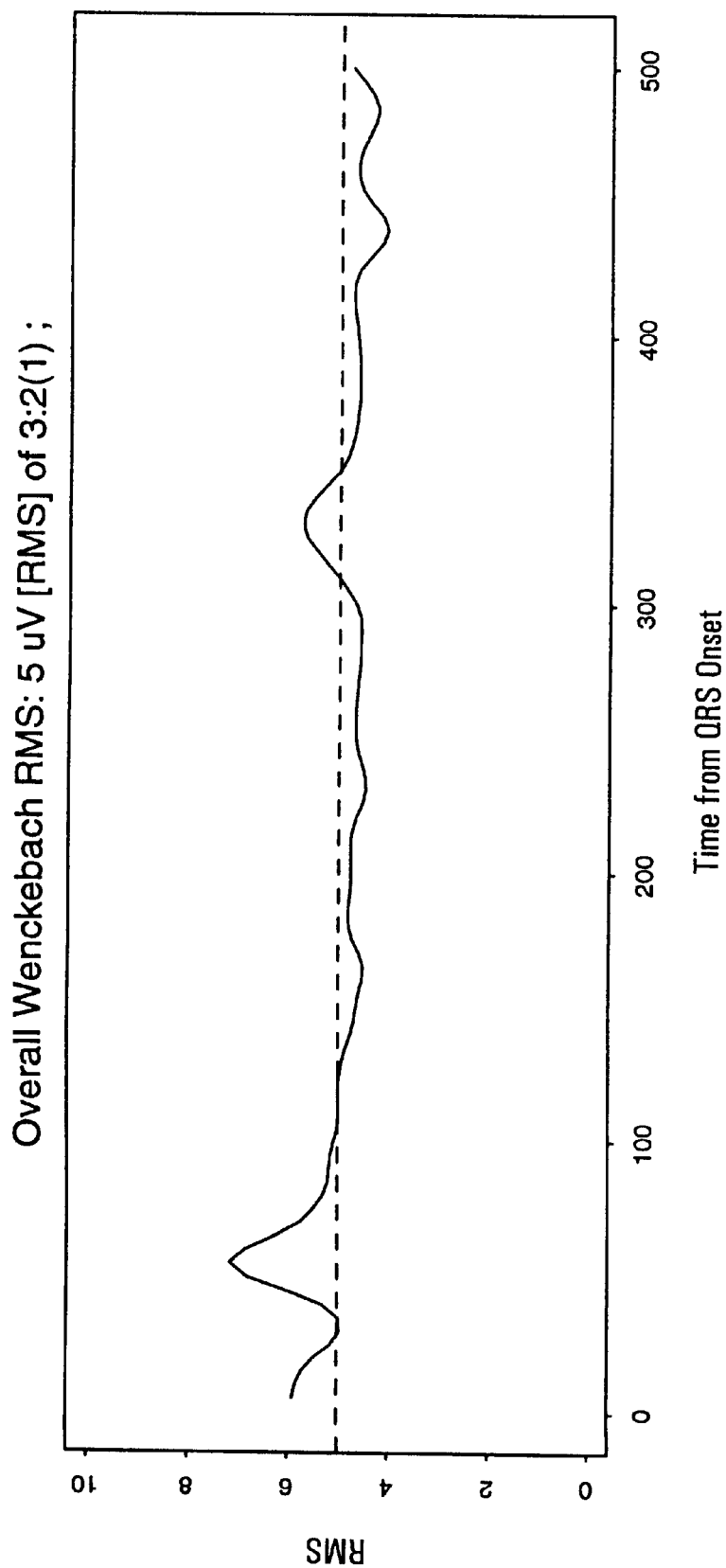
FIG. 12 shows the estimated overall RMS amplitude for all Wenckebach activity of the illustrative run of FIG. 5; a simulated 5 microvolts RMS 3:2 Wenckebach pattern has been added to the BSP data.

From the mode strength vector x, the overall and individual mode root mean squared (RMS) Wenckebach amplitude values are also computed. Again, this is done for all time bins from QRS onset to 500 msec. after. The RMS values for the 3:N modes are shown in FIG. 11 while the overall Wenckebach RMS amplitude is shown in FIG. 12. The mode strengths fairly accurately estimate the RMS amplitude of the Wenckebach activity at 5 microvolts.

The technique of the present invention is applicable for detecting possibly complex intramyocardial Wenckebach activity, i.e., Wenckebach signal with two or more Wenckebach phases and modes. The above analysis of a 3:2

Wenckebach pattern is shown for illustrative purposes only, not as a limit to the scope of application of the present invention.

Although the preferred embodiment of the present invention has been described and illustrated in detail, it is to be understood that a person skilled in the art can make modifications within the scope of the invention.

What is claimed is:

1. An apparatus for detecting repeating patterns of anomalous Intramyocardial electrical activity in the heart of a patient, comprising:
   (a) means for obtaining data on an electrical potential that includes a cardiac component and a respiratory component;
   (b) means for obtaining respiratory data from the body; and
   (c) processor electrically associated with the means for obtaining electrical potential data and with the means for obtaining respiratory data, the processor regressing the electrical potential data on the respiratory data to estimate the respiratory component in the electrical potential, said processor aligning the electrical potential data by heart beats and statistically modeling the respiratory data with the electrical potential data in alignment across multiple heart beats the processor also determining whether anomalous Intramyocardial activity is present by finding the difference between the electrical potential data and the estimated respiratory component.

2. The apparatus according to claim 1 wherein the processor determines whether intramyocardial anomaly is present, including:
   (a) in the processor storing data of a nonsingular Wenckebach matrix W corresponding to Wenckebach patterns of cardiac activity; and
   (b) the processor calculating a vector of Wenckebach basis function strengths x based on the nonsingular Wenckebach matrix W and the electrical potential data, the Wenckebach basis function strengths indicating the presence or absence of periodically repeated anomalies in said difference.

3. The apparatus according to claim 2 wherein the processor calculates the Wenckebach basis fuinction strengths via a relationship describing the electrical potential data as including Wenckebach activity being additive to respiratory interference, in the relationship the nonsingular Wenckebach matrix W acts on the vector of Wenckebach basis function strengths x to describe said difference between the electrical potential data and the estimated respiratory data, in the relationship the Wenckebach basis function strengths are expressed in terms of said difference between the electrical potential data and the estimated respiratory data and in terms of a function of the nonsingular Wenckebach matrix W, the Wenckebach basis function strengths allowing determination of presence or absence of effect in the electrical potential data caused by repeating patterns of anomalous intramyocardial Wenckebach activity.

4. The apparatus according to claim 2 wherein the processor orthogonalizes a singular matrix representing Wenckebach patterns to remove singularity therefrom to obtain the nonsingular Wenckebach matrix W.

5. The apparatus according to claim 2 wherein the means for obtaining respiratory data comprises electrodes for sensing body surface potential (BSP) signal and deriving both the electrical potential and the respiratory data from the BSP signal.

6. The apparaus according to claim 2, wherein the processor calculates the vector of Wenckebach basis function strengths x by a relationship in which the nonsingular Wenckebach matrix W, a vector b of cardiac electrical potential data obtained from the electrical potential data after reducing respiratory effect by regressing, and the vector of Wenckebach basis function strengths x are related by $x=W^I b$, where the $W^I$ represents the generalized inverse of the matrix W.

7. The apparatus according to claim 6, wherein the processor tests the respiratory data to determine the presence or absence of periodically repeated Wenckebach-like activity in the respiratory data to assess the risk of mistakenly inferring Wenckebach anomaly in said difference, wherein the processor for said testing performs calculation, including: obtaining respiratory data points by extracting from the respiratory data according to heart beat times in the electrical potential data, calculating values of Wenckebach basis function strengths x based on the extracted respiratory data points and the nonsingular Wenckebach matrix W, and calculating a generalized likelihood ratio (GLR), wherein small values in the GLR will indicate the absence of periodically repeating Wenckebach-like activity in the respiratory data.

8. The apparatus according to claim 1, wherein the means for obtaining electrical potential data comprises electrodes for detecting body surface electrical potentials (BSP) from the body of the patient.

9. The apparatus according to claim 8, further comprising one or more filters to filter the BSP to remove noise, which includes non-respiratory physiologically generated electrical noise, to obtain the electrical potential data used for regressing.

10. The apparatus according to claim 8, wherein the processor has a digital filter embodied by a computer program having code means for filtering data from the BSP signal.

11. A method for detecting repeating patterns of anomalous Intramyocardial activity, comprising:
   (a) providing electrical potential data that include a cardiac component and a respiratory component;
   (b) regressing the electrical potential data on respiratory data to estimate the respiratory component, by aligning the electrical potential data by heart beats and statistically modeling the respiratory data with the electrical potential data in alignment across multiple heart beats; and
   (c) determining the presence or absence of intramyocardial anomaly by finding the difference between the electrical potential data and the estimated respiratory component and detecting periodically repeating intramyocardial anomaly in the difference.

12. The method according to claim 11 wherein the step of determining intramyocardial anomaly includes the steps of:
   (a) generating a nonsingular Wenckebach matrix W describing patterns Wenckebach activity; and
   (b) calculating a vector of Wenckebach basis finction strengths x based on the nonsingular Wenckebach matrix W and the regressed electrical potential data to determine the presence or absense of repeating patterns of anomalous intramyocardial activity, the vector of Wenckebach basis function strengths x indicating the intensity of Wenckebach activity.

13. The method according to claim 12 wherein the Wenckebach basis function strengths x are calculated via a relationship that describes the electrical potential data as including data due to Wenckebach activity being additive to data due to respiratory interference, in the relationship the nonsingular Wenckebach matrix W acts on the vector of Wenckebach basis function strengths x to describe said difference between the electrical potential data and the estimated respiratory interference, in the relationship expressing the Wenckebach basis function strengths in terms of a function of the nonsingular Wenckebach matrix W and said difference between the electrical potential data and the estimated respiratory interference.

14. The method according to claim 12, wherein the nonsingular Wenckebach matrix W is obtained by orthogonalizing a singular Wenckebach matrix describing phases of modes of Wenckebach activity.

15. The method according to claim 12, wherein the nonsingular Wenckebach matrix W, a vector b of values of the difference between the electrical potential data and the estimated respiratory component, and the Wenckebach basis function strengths in x are related by $x=W^I b$, where $W^I$ represents generalized inverse of the matrix W.

16. The method according to claim 15 further comprising determining a generalized likelihood ratio (GLR), said GLR being the power in b due to Wenckebach activity divided by the power in b not due to Wenckebach activity, the value of said GLR being indicative of whether Wenckebach activity has been reliably detected and hence whether x is a reliable estimate of the amplitude of Wenckebach activity.

17. The method according to claim 12, wherein the estimated respiratory component is estimated using an equation having an indicator function indicating respiratory phases including inspiration, expiration, and rest of the corresponding respiratory data.

18. The method according to claim 12, further comprising performing singular value decomposition on a larger Wenckebach matrix $\tilde{W}$ to obtain the nonsingular Wenckebach matrix W.

19. The method according to claim 12, wherein the step of regressing includes regressing the BSP data on more than one set of respiratory data obtained from different sites on the patient.

20. The method according to claim 11, further comprising filtering BSP signal detected from the body of the patient to remove electromagnetic interference and non-respiratory physiologically generated electrical interference.

21. The method according to claim 20, further comprising filtering BSP signal to remove at least one physiologically generated electrical interference selected from the group consisting of regular electrocardiographic signal, muscle tremor noise, and electrogastric signal.

22. The method according to claim 11 further comprising:
    (a) measuring body surface potential (BSP) signal from the body of the patient and determining the electrical potential from the BSP signal;
    (b) filtering the BSP signal to remove noise including a non-respiratory physiologically generated electrical noise to obtain the electrical potential data used for regressing; and
    (c) obtaining the respiratory data.

23. The method according to claim 12 further comprising a step for testing the respiratory data to determine the presence or absence of periodic activity to indicate the risk of mistakenly inferring the presence of Wenckebach anomalies in said difference, the step of testing including obtaining data points by extracting from the respiratory data according to time of heart beats in the electrical potential data, acting on the extracted data points with the nonsingular Wenckebach matrix W to obtain the Wenckebach basis function strengths x, the step of testing further comprising calculating a generalized likelihood ratio (GLR) based on W and x wherein small values in the GLR will indicate the absence of Wenckebach-like interference in the respiratory data.

24. The apparatus according to claim 1 wherein the electrical potential data comprises data in time-series and the processor arranges by alignment of heart beats such that each heart beat has points in time in the time-series corresponding to points in time in the time-series of other heart beats and the respiratory data are modeled with data sets from the electrical potential data, each of said sets spanning multiple heart beats at a point in time on the aligned heart beats, each set having a different point in time.

25. The apparatus according to claim 24 wherein the means for obtaining respiratory data obtains two or more sets of respiratory data, each set spanning substantially the same time period and wherein the processor models each set of respiratory data with the electrical potential data to estimate the respiratory component of the electrical potential data.

26. The method according to claim 11 wherein the electrical potential data comprises data in time-series and the regression-analyzing step comprises arranging the electrical potential data by alignment of heart beats such that each heart beat has points in time in the time-series corresponding to points in time in the time-series of other heart beats and the regression-analyzing step further comprises modeling the respiratory data with data sets from the electrical potential data, wherein each of said sets spans multiple heart beats at a point in time on the aligned heart beats, each set having a different point in time.

27. An apparatus for detecting repeating patterns of anomalous intramyocardial electrical activity in the heart of a patient, comprising:
    (a) means for obtaining data on an electrical potential that includes a cardiac component and a respiratory component;
    (b) means for obtaining respiratory data from the body; and
    (c) processor electrically associated with the means for obtaining electrical potential data and with the means for obtaining respiratory data, the processor regressing the electrical potential data on the respiratory data to estimate the respiratory component in the electrical potential, the processor also determining whether anomalous intramyocardial activity is present by finding the difference between the electrical potential data and the estimated respiratory component, wherein the processor calculates the vector of Wenckebach basis function strengths x by a relationship in which the nonsingular Wenckebach matrix W, a vector b of cardiac electrical potential data obtained from the electrical potential data, and the vector of Wenckebach basis function strengths x are related by $x=W^I b$, where the $W^I$ represents the generalized inverse of the matrix W.

28. An article of manufacture comprising a program storage medium, tangibly embodying a program code means readble by a computer to cause the computer to analyze for repeating patterns of anomalous intramyocardial activity of a patient, the computer readable program code means in the article of manufacture including:
    (a) code means for regressing electrical potential data of the patient on respiratory data of the patient to estimate a respiratory component in the electrical potential data, the electrical potential data including a cardiac component and a respiratory component;
    (b) code means for generating a vector b by determining the difference between the electrical potential data and the estimated respiratory component;

(c) code means for generating a nonsingular Wenckebach matrix W describing patterns of Wenckebach activity; and (d) code means for determining a vector of Wenckebach basis function strengths x based on the nonsingular Wenckebach matrix W and the vector b of said difference to determine the presence or absence of repeating patterns of Wenckebach activity, wherein the vector of Wenckebach basis finction strengths x indicating the intensity of Wenckebach activity.

* * * * *